United States Patent
Williams et al.

(10) Patent No.: US 11,104,663 B2
(45) Date of Patent: Aug. 31, 2021

(54) CIPROFLOXACIN POLYMORPH AND ITS USE

(71) Applicant: CRITITECH, INC., Lawrence, KS (US)

(72) Inventors: Mark Williams, Lawrence, KS (US); Jacob Sittenauer, Lawrence, KS (US); Shelby Clark, Lawrence, KS (US); Joseph Farthing, Lawrence, KS (US); Michael Baltezor, Lawrence, KS (US); Matthew McClorey, Lawrence, KS (US)

(73) Assignee: CritiTech, Inc., Lawrence, KS (US)

( * ) Notice: Subject to any disclaimer, the term of this patent is extended or adjusted under 35 U.S.C. 154(b) by 0 days.

(21) Appl. No.: 16/650,670

(22) PCT Filed: Sep. 28, 2018

(86) PCT No.: PCT/US2018/053336
§ 371 (c)(1),
(2) Date: Mar. 25, 2020

(87) PCT Pub. No.: WO2019/067851
PCT Pub. Date: Apr. 4, 2019

(65) Prior Publication Data
US 2020/0247780 A1    Aug. 6, 2020

Related U.S. Application Data

(60) Provisional application No. 62/730,828, filed on Sep. 13, 2018, provisional application No. 62/566,042, filed on Sep. 29, 2017.

(51) Int. Cl.
*C07D 401/10* (2006.01)
*A61K 9/14* (2006.01)
*A61K 9/00* (2006.01)
*A61P 31/04* (2006.01)

(52) U.S. Cl.
CPC .......... *C07D 401/10* (2013.01); *A61K 9/0073* (2013.01); *A61K 9/14* (2013.01); *A61P 31/04* (2018.01)

(58) Field of Classification Search
CPC .......... C07D 401/10; A61K 9/14; A61K 9/00; A61P 31/04
USPC ....................................................... 424/489
See application file for complete search history.

(56) References Cited

U.S. PATENT DOCUMENTS 5,833,891 A    11/1998    Subramaniam et al.

FOREIGN PATENT DOCUMENTS

WO    2016/004231    1/2016

OTHER PUBLICATIONS

The International Search Report (ISR) with Written Opinion for PCT/US2018/053336 dated Nov. 29, 2018, pp. 1-17.
Mahapatra, Sudarshan et al. "A Device to Crystallize Organic Solids: Structure of Ciprofloxacin, Midazolam, and Ofloxacin as Targets" Crystal Growth & Design (2010) vol. 10(4), pp. 1866-1870.
Tehler, Ulrika et al. "Optimizing Solubility and Permeability of a Biopharmaceutics Classification System {BCS} Class-4 Antibiotic Drug Using lipophilic Fragments Disturbing the Crystal Lattice" Journal of Medicinal Chemistry (2013) vol. 56(6), pp. 2690-2694.
Bergstrom, Christel A.S. et al. "Experimental and Computational Screening Models for Prediction of Aqueous Drug Solubility" Pharmaceutical Research (2002) vol. 19(2), pp. 182-188.

*Primary Examiner* — Tracy Vivlemore
*Assistant Examiner* — Ebenezer O Sackey
(74) *Attorney, Agent, or Firm* — McDonnell Boehnen Holbert & Berghoff LLP

(57) ABSTRACT

The present disclosure relates to ciprofloxacin polymorphs and their use in treating infections.

19 Claims, 17 Drawing Sheets

FIGURE 1
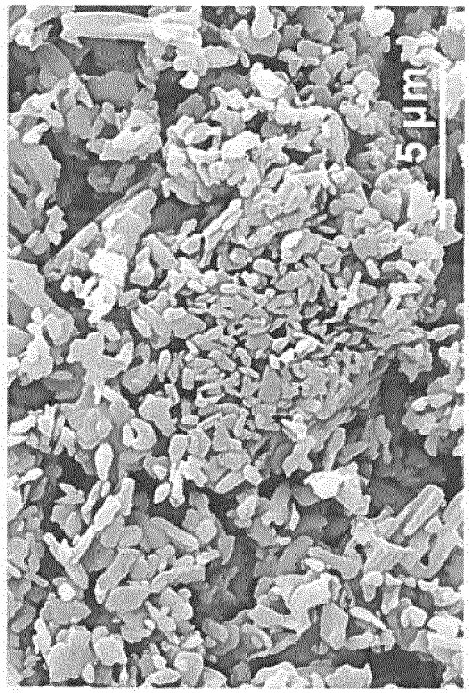
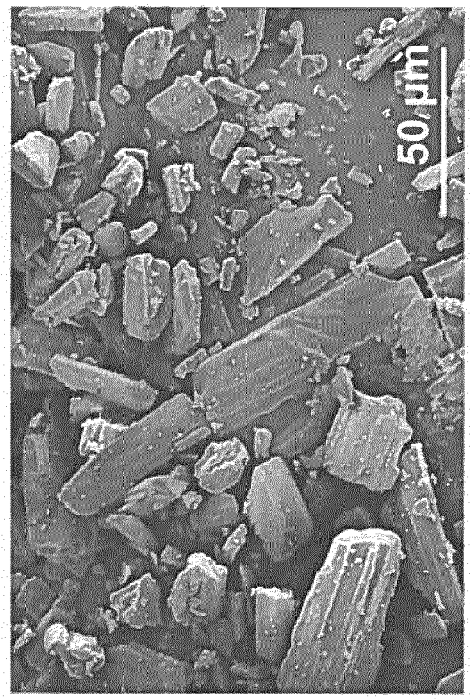

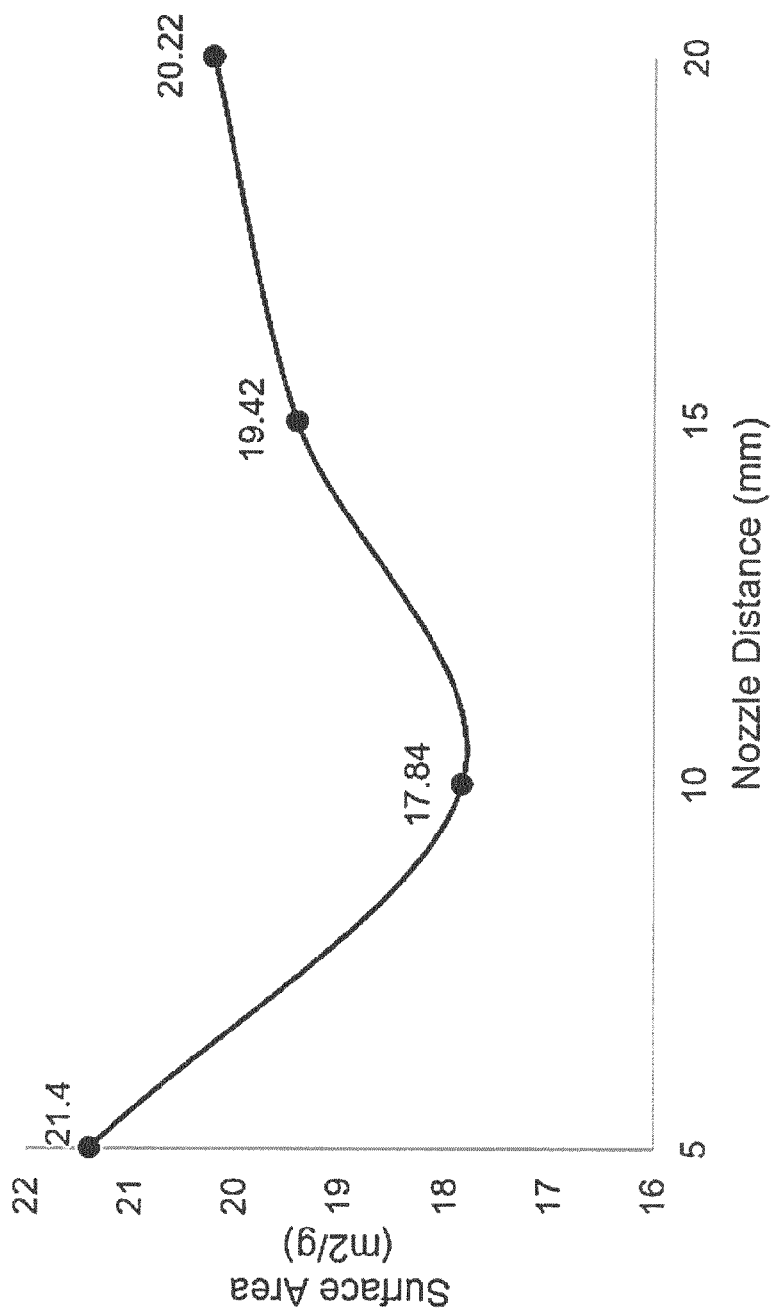

CIPROFLOXACIN POLYMORPH AND ITS USE

CROSS REFERENCE

This application is a U.S. national phase of International Application No. PCT/US2018/053336, filed on Sep. 28, 2018, which claims priority to U.S. Provisional Application No. 62/730,828, filed Sep. 13, 2018; and U.S. Provisional Application No. 62/566,042, filed Sep. 29, 2017, all of which are incorporated by reference herein in their entirety.

BACKGROUND OF THE DISCLOSURE

Persistent respiratory tract infections caused by a variety of microorganisms can lead to decline in lung function, frequent hospitalization, and/or a general decline in health, particularly for patients with cystic fibrosis (CF), non-CF bronchiectasis, pulmonary fibrosis (PF), and Chronic Obstructive Pulmonary Disease (COPD). Delivering an antibiotic as an inhaled aerosol would be an efficient way to provide the drug to the respiratory tract, which is the primary site of infection, and reduce the side effect associated with higher doses of the drug.

SUMMARY OF THE DISCLOSURE

One aspect of the disclosure provides a polymorph of ciprofloxacin (1-cyclopropyl-6-fluoro-4-oxo-7-(piperazin-1-yl)-1,4-dihydroquinoline-3-carboxylic acid; or ciprofloxacin free base) characterized in that it provides a X-ray powder diffraction (XRPD) pattern comprising a peak at about 9.0 (2θ degrees); or comprising a peak at 9.0±0.1 (2θ degrees). In another aspect of the disclosure, a polymorph of ciprofloxacin is characterized in that it provides an XRPD pattern in accordance with that shown in FIG. 6. In another aspect of the disclosure, a polymorph of ciprofloxacin is characterized in that it provides an XRPD pattern comprising peaks substantially as set out in Table 4. XRPD data as disclosed herein was obtained by standard techniques using Seimens D5000 diffractometer operating with a Cu Kα radiation source at 40 kW, 35 mA, step size 0.02° 2θ, and a continuous scan at a rate of 2° 2θ/minute.

Another aspect of the disclosure provides a polymorph of ciprofloxacin characterized in that it provides a Fourier-transform infrared spectroscopy (FTIR) spectrum comprising peaks at about 1724 $cm^{-1}$, about 1704 $cm^{-1}$, about 1627 $cm^{-1}$, about 1455 $cm^{-1}$, about 1254 $cm^{-1}$, about 1213 $cm^{-1}$, about 1202 $cm^{-1}$, about 1186 $cm^{-1}$, about 1061 $cm^{-1}$, about 947 $cm^{-1}$, about 880 $cm^{-1}$, about 746 $cm^{-1}$, about 665 $cm^{-1}$, and about 633 $cm^{-1}$; or comprising peaks at 1724±4 $cm^{-1}$, 1704±4 $cm^{-1}$, 1627±4 $cm^{-1}$, 1455±4 $cm^{-1}$, 1254±4 $cm^{-1}$, 1213±4 $cm^{-1}$, 1202±4 $cm^{-1}$, 1186±4 $cm^{-1}$, 1061±4 $cm^{-1}$, 947±4 $cm^{-1}$, 880±4 $cm^{-/}$, 746±4 $cm^{-1}$, 665±4 $cm^{-1}$, and 633±4 $cm^{-1}$. In another aspect of the disclosure, a polymorph of ciprofloxacin is characterized in that it provides an FTIR spectrum in accordance with that shown in FIG. 10. FTIR spectral data as disclosed herein was obtained by standard techniques using Shimadzu MIRacle 10 FTIR spectrometer in attenuated total reflectance (ATR) mode operating at a total of 32 scans with a resolution of 4 $cm^{-1}$.

Another aspect of the disclosure provides a polymorph of ciprofloxacin characterized in that it provides a differential scanning calorimetry (DSC) profile having an endothermic peak at about 266° C. In certain embodiments, ciprofloxacin characterized in that it provides a differential scanning calorimetry (DSC) profile having an endothermic peak at 266±4° C.

Another aspect of the disclosure provides particles comprising, consisting essentially of, or consisting of the polymorph of the disclosure as described herein.

Another aspect of the disclosure provides compositions including the polymorph of the disclosure as described herein. For example, the disclosure provides a composition including particles that comprise the polymorph of the disclosure.

Another aspect of the disclosure provides pharmaceutical compositions including the polymorph of the disclosure as described herein or the particles as described herein, and one or more pharmaceutically acceptable carriers.

Another aspect of the disclosure provides methods for treating a bacterial infection including administering to a subject in need thereof the polymorph of the disclosure as described herein, or the particles as described herein, or the composition of the disclosure as described herein, or the pharmaceutical composition of the disclosure as described herein, in an amount efficient to treat the infection.

Another aspect of the disclosure provides methods for preparing the polymorph of the disclosure as provided herein, including:
  (a) obtaining a solution or a suspension of 1-cyclopropyl-6-fluoro-4-oxo-7-(piperazin-1-yl)-1,4-dihydroquinoline-3-carboxylic acid in a solvent or mixture of solvents; and
  (b) removing the solvent or mixture of solvents from said solution or suspension to form the polymorph particles.

Another aspect of the disclosure provides methods for preparing the polymorph particles of the disclosure as provided herein, including:
  (a) obtaining a solution or a suspension of 1-cyclopropyl-6-fluoro-4-oxo-7-(piperazin-1-yl)-1,4-dihydroquinoline-3-carboxylic acid in a solvent or mixture of solvents;
  (b) feeding and spraying said solution or suspension into a pressurized chamber to obtain a stream of atomized droplets; and
  (c) removing the solvent or mixture of solvents from said droplets to form the polymorph particles.

Another aspect of the disclosure provides a polymorph prepared by the methods of the disclosure as provided herein.

BRIEF DESCRIPTION OF THE DRAWINGS

The accompanying drawings are included to provide a further understanding of the compositions and methods of the disclosure, and are incorporated in and constitute a part of this specification. The drawings are not necessarily to scale, and sizes of various elements may be distorted for clarity. The drawings illustrate one or more embodiment(s) of the disclosure, and together with the description serve to explain the principles and operation of the disclosure.

FIG. 1 provides electron micrograph of ciprofloxacin hydrochloride (1-cyclopropyl-6-fluoro-4-oxo-7-(piperazin-1-yl)-1,4-dihydroquinoline-3-carboxylic acid hydrochloride salt; or ciprofloxacin HCl) particles. (A) shows raw (unprocessed) material before any methods of the disclosure; and (B) shows the processed particles obtained using the method provided in Example 1.

DETAILED DESCRIPTION

Figure 2:
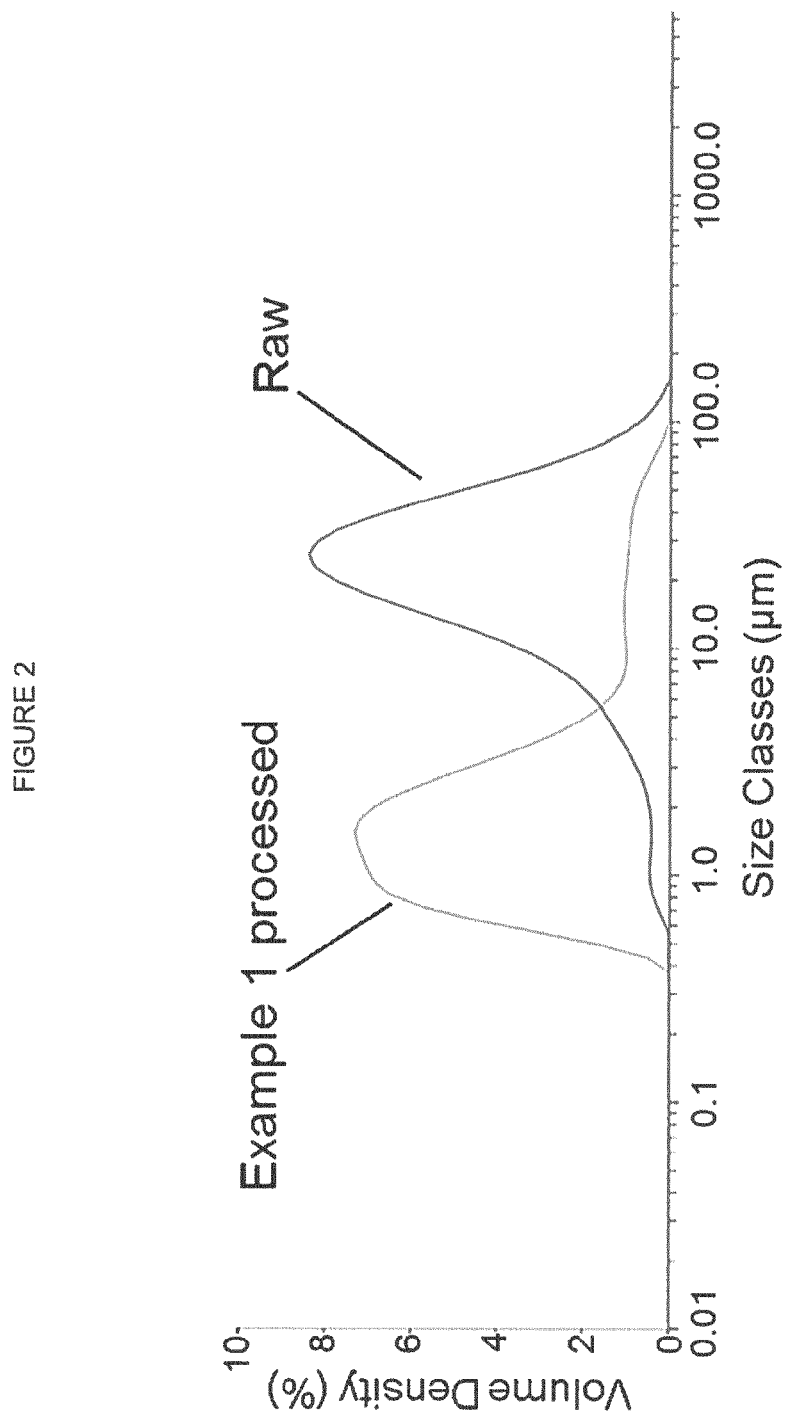
FIG. 2 is a graph illustrating particle size distribution of raw (unprocessed) ciprofloxacin hydrochloride and the processed ciprofloxacin hydrochloride particles obtained using the method of Example 1.
Figure 3A:
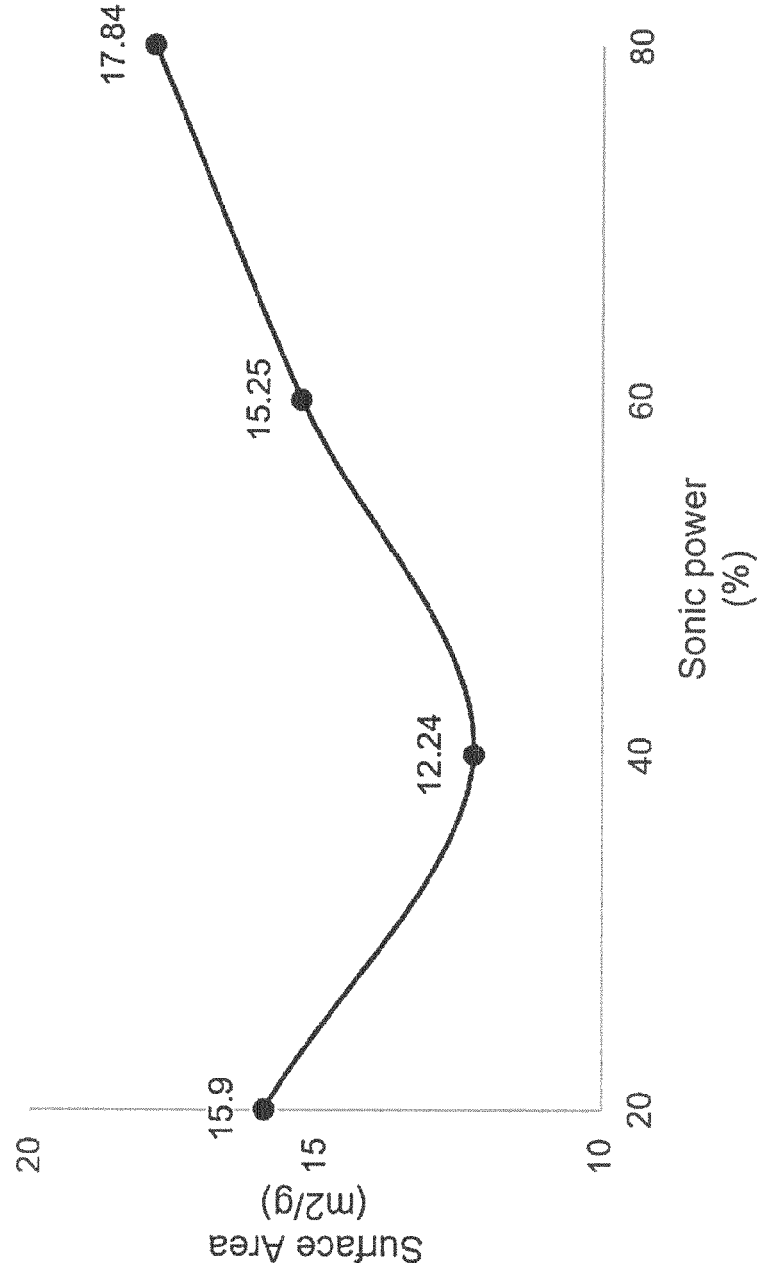
FIG. 3 illustrates the effect of different (A) sonic power (%), (B) nozzle diameter (µm), and (C) distance of the nozzle from the sonic probe (mm) on the surface area ($m^2/g$) of processed ciprofloxacin hydrochloride particles obtained in Example 1.
Figure 3B:
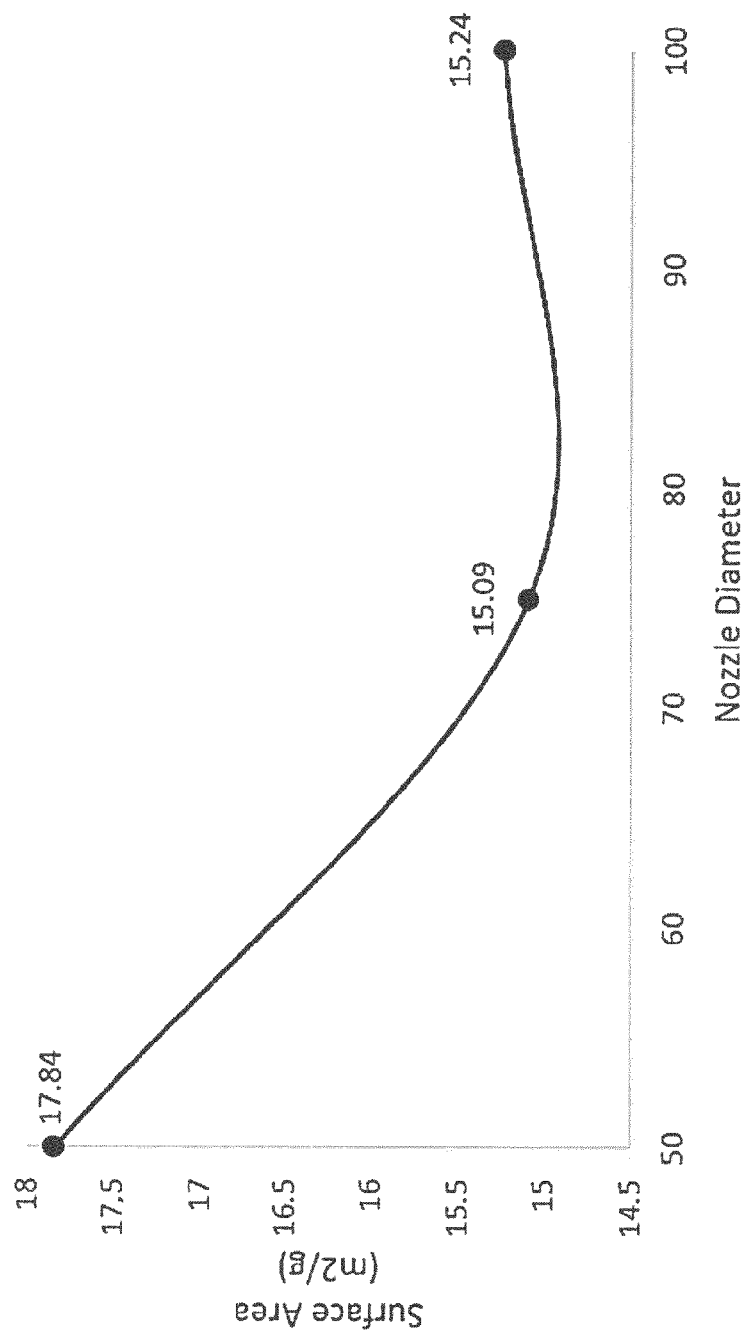

The particulars shown herein are by way of example and for purposes of illustrative discussion of the preferred embodiments of the present disclosure only and are presented in the cause of providing what is believed to be the most useful and readily understood description of the principles and conceptual aspects of various embodiments of the disclosure. In this regard, no attempt is made to show structural details of the disclosure in more detail than is necessary for the fundamental understanding of the disclosure, the description taken with the drawings and/or examples making apparent to those skilled in the art how the several forms of the disclosure may be embodied in practice. Thus, before the disclosed compositions and methods are described, it is to be understood that the aspects described herein are not limited to specific embodiments, or configurations, and as such can, of course, vary. It is also to be understood that the terminology used herein is for the purpose of describing particular aspects only and, unless specifically defined herein, is not intended to be limiting. All embodiments of any aspect of the disclosure can be used in combination, unless the context clearly dictates otherwise.

As used herein, the singular forms "a", "an" and "the" include plural referents unless the context clearly dictates otherwise. "And" as used herein is interchangeably used with "or" unless expressly stated otherwise.

As used herein, "about" means±five percent (5%) of the recited unit of measure.

Unless the context clearly requires otherwise, throughout the description and the claims, the words 'comprise', 'comprising', and the like are to be construed in an inclusive sense as opposed to an exclusive or exhaustive sense; that is to say, in the sense of "including, but not limited to". Words using the singular or plural number also include the plural and singular number, respectively. Additionally, the words "herein," "above," and "below" and words of similar import, when used in this application, shall refer to this application as a whole and not to any particular portions of the application. The compositions and methods for their use can "comprise," "consist essentially of," or "consist of" any of the ingredients or steps disclosed throughout the specification.

The ability of a compound to exist in different crystal structures is known as polymorphism. As used herein "polymorph" refers to crystalline forms having the same chemical composition but different spatial arrangements of the molecules, atoms, and/or ions forming the crystal. While polymorphs have the same chemical composition, they differ in packing and geometrical arrangement, and may exhibit different physical properties such as melting point, shape, color, density, hardness, deformability, stability, dissolution, and the like. Polymorphs of a compound can be distinguished in a laboratory by X-ray diffraction spectroscopy, such as XRPD, and by other methods, such as infrared spectrometry (IR). Additionally, polymorphs of the same drug substance or active pharmaceutical ingredient can be administered by itself or formulated as a drug product (pharmaceutical composition) and are well known in the pharmaceutical art to affect, for example, the solubility, stability, flowability, tractability and compressibility of drug substances and the safety and efficacy of drug products (see Brittain, H. (Ed.). (1999). *Polymorphism in Pharmaceutical Solids*. Boca Raton: CRC Press; and Hilfiker, Rolf (ed.). (2006) *Polymorphism in the Pharmaceutical Industry*. Weinheim, Germany: Wiley-VCH).

In general, the various aspects and embodiments of the disclosure provide novel ciprofloxacin polymorphs that, in various embodiments, are effective in treatment of respiratory infections, while providing fewer side effects. The inventors have also found that, in certain embodiments, a novel polymorph of ciprofloxacin (referred to herein as "Form A") has significantly slower rate of dissolution in water than conventional (i.e., raw, unprocessed) ciprofloxacin (referred to herein as "Form B") and conventional (i.e., raw, unprocessed) ciprofloxacin hydrochloride. In addition, ciprofloxacin polymorph Form A, when administered to the lung, had similar concentration in plasma but significantly higher concentrations and longer residence in the lung than ciprofloxacin hydrochloride particles of Example 1 administered to the lung or i.v. administered ciprofloxacin formulation.

Thus, one aspect of the disclosure provides a novel polymorph of ciprofloxacin herein identified as Form A. The polymorph of ciprofloxacin of the disclosure is characterized in that it provides a XRPD pattern comprising a peak at about 9.0 (2θ degrees). In certain embodiments of the ciprofloxacin polymorph of the disclosure, the XRPD pattern further includes peaks at about 23.2 and about 26.9 (2θ degrees). In certain embodiments of the ciprofloxacin polymorph of the disclosure, the XRPD pattern further includes peaks at about 9.3, about 18.7, and/or about 27.6 (2θ degrees). XRPD data as disclosed herein was obtained by standard techniques using Seimens D5000 diffractometer operating with a Cu Kα radiation source at 40 kW, 35 mA, step size 0.02° 2θ, and a continuous scan at a rate of 2° 2θ/minute.

In certain embodiments, the ciprofloxacin polymorph of the disclosure is characterized in that it provides a XRPD pattern comprising a peak at 9.0±0.1 (2θ degrees). In certain embodiments of the ciprofloxacin polymorph of the disclosure, the XRPD pattern further includes peaks at 23.2±0.1 and/or 26.9±0.1 (2θ degrees). In certain embodiments of the ciprofloxacin polymorph of the disclosure, the XRPD pattern further includes peaks at 9.3±0.1, 18.7±0.1, and/or 27.6±0.1 (2θ degrees).

In certain embodiments, the ciprofloxacin polymorph of the disclosure is characterized in that it provides an XRPD pattern in accordance with that shown in FIG. 6.

In certain embodiments, the ciprofloxacin polymorph of the disclosure is characterized in that it provides an XRPD pattern comprising peaks substantially as set out in Table 4.

The polymorph of ciprofloxacin of the disclosure, in certain embodiments, is characterized in that it provides a FTIR spectrum comprising peaks at about 1724 $cm^{-1}$, about 1704 $cm^{-1}$, about 1627 $cm^{-1}$, about 1455 $cm^{-1}$, about 1254 $cm^{-1}$, about 1213 $cm^{-1}$, about 1202 $cm^{-1}$, about 1186 $cm^{-1}$, about 1061 $cm^{-1}$, about 947 $cm^{-1}$, about 880 $cm^{-1}$, about 746 $cm^{-1}$, about 665 $cm^{-1}$, and about 633 $cm^{-1}$. In certain embodiments, the ciprofloxacin polymorph of the disclosure is characterized in that it provides a FTIR spectrum comprising peaks at 1724±4 $cm^{-1}$, 1704±4 $cm^{-1}$, 1627±4 $cm^{-1}$, 1455±4 $cm^{-1}$, 1254±4 $cm^{-1}$, 1213±4 $cm^{-1}$, 1202±4 $cm^{-1}$, 1186±4 $cm^{-1}$, 1061±4 $cm^{-1}$, 947±4 $cm^{-1}$, 880±4 $cm^{-1}$, 746±4 $cm^{-1}$, 665±4 $cm^{-1}$, and 633±4 $cm^{-1}$. FTIR spectral data as disclosed herein was obtained by standard techniques using Shimadzu MIRacle 10 FTIR spectrometer in attenuated total reflectance (ATR) mode operating at a total of 32 scans with a resolution of 4 $cm^{-1}$.

The polymorph of ciprofloxacin of the disclosure, in certain embodiments, is characterized in that it provides an FTIR spectrum in accordance with that shown in FIG. 10.

In certain embodiments, the ciprofloxacin polymorph of the disclosure is characterized in that it provides a differential scanning calorimetry (DSC) profile having an endothermic peak at about 266° C. In certain embodiments, ciprofloxacin characterized in that it provides a differential scanning calorimetry (DSC) profile having an endothermic peak at 266±4° C.

Another aspect of the disclosure provides particles comprising, consisting essentially of, or consisting of, the ciprofloxacin polymorph of the disclosure as described herein. For example, in certain embodiments, the particles of the disclosure as described herein may include at least 5%, at least 10%, at least 20%, at least 30%, at least 40%, at least 50%, or at least 60%, or at least 75%, or at least 80%, or at least 90%, or at least 95%, or at least 97%, or at least 98%, or at least 99%, or at least 99.8%, or even 100% by weight of the ciprofloxacin polymorph of the disclosure as described herein.

In certain embodiments, the particles of the disclosure have a mean particle size (volume-based distribution) in the range of about 0.5 μm to about 20 μm. For example, in certain embodiments, the particles of the disclosure have a mean particle size (volume-based distribution) in the range of about 0.5 μm to about 10 μm, or about 0.5 μm to about 8 μm, or about 0.5 μm to about 5 μm, or about 1 μm to about 15 μm, or about 1 μm to about 10 μm, or about 1 μm to about 8 μm, or about 1 μm to about 5 μm. In certain embodiments, the particles of the disclosure have a mean particle size (volume-based distribution) in the range of 1 μm to about 5 μm.

As the person of ordinary skill in the art will appreciate, the particle size distribution can be characterized by d50, d10 and d90 values, where d50 is the median particle size, d10 is the particle size at the $10^{th}$ percentile of particles ranked by size, and d90 is the particle size at the $90^{th}$ percentile of particles ranked by size. In certain embodiments of the particles as otherwise described herein, the particle has a median particle size (i.e., d50, $50^{th}$ percentile particle size) of about 0.5 to about 10 μm. In certain embodiments as otherwise described herein, the particle has a median particle size (i.e., d50, $50^{th}$ percentile particle size) of about 1 to about 10 μm, or about 3 to about 10 μm, or about 5 to about 10 μm, or about 7 to about 10 μm, or about 1 to about 5 μm, or about 2 to about 5 μm, or about 3 to about 5 μm, or about 3 to about 7 μm, or about 3 to about 6 μm.

The distribution of particle sizes in a particulate material can affect the bioavailability and also have an effect on particulate material's flowability. Thus, for pharmaceutical applications (e.g., powder dosage forms) the particle size distribution of the particulate drug is important. Here, the present inventors have determined that use of particles with relatively narrow particle size distribution can provide the desired therapeutic benefits, particularly when administered by inhalation or nebulization. Thus, in certain embodiments of the disclosure, the particles may have a relatively narrow particle size distribution, for example, as compared to the conventional particles. For example, the ciprofloxacin polymorph particles obtained in Example 2 showed a d10 and a d90 value of 1.19 μm to 13.3 μm, whereas unprocessed, raw ciprofloxacin showed a d10 and a d90 value of 1.44 μm to 244 μm. Thus, in certain embodiments, the particle has a d10 and a d90 value (i.e., $10^{th}$ percentile particle size and $90^{th}$ percentile particle size) within the range of about 0.3 to about 20 μm, or about 0.5 to about 20 μm, or about 1 to about 20 μm, or about 3 to about 20 μm, or about 5 to about 20 μm, or about 0.5 to about 15 μm, or about 1 to about 15 μm, or about 3 to about 15 μm, or about 5 to about 15 μm, or about 0.5 to about 10 μm, or about 1 to about 10 μm, or about 3 to about 10 μm, or about 1 to about 13 μm, or about 3 to about 13 μm. Particle sizes as described herein are measured by laser diffraction, e.g., as in a Malvern Mastersizer 3000 Particle Analyzer.

The particles of the disclosure may be dry powders or aerosolized for administration, and the mass median aerodynamic diameter (MMAD) of the aerosol droplets of the particles of the disclosure or suspensions thereof may be any suitable diameter for use in the disclosure. In one embodiment, the particle aerosol droplets have a MMAD of between about 0.5 μm to about 6 μm diameter. In various further embodiments, the dry powders of the aerosol droplets have a MMAD in the range of about 0.5 μm to about 5.5 μm diameter, about 0.5 μm to about 5 μm diameter, about 0.5 μm to about 4.5 μm diameter, about 0.5 μm to about 4 μm diameter, about 0.5 μm to about 3.5 μm diameter, about 0.5 μm to about 3 μm diameter, about 0.5 μm to about 2.5 μm diameter, about 0.5 μm to about 2 μm diameter, about 1 μm to about 5.5 μm diameter, about 1 μm to about 5 μm diameter, about 1 μm to about 4.5 μm diameter, about 1 μm to about 4 μm diameter, about 1 μm to about 3.5 μm diameter, about 1 μm to about 3 μm diameter, about 1 μm to about 2.5 μm diameter, about 1 μm to about 2 μm diameter, about 1.5 μm to about 5.5 μm diameter, about 1.5 μm to about 5 μm diameter, about 1.5 μm to about 4.5 μm diameter, about 1.5 μm to about 4 μm diameter, about 1.5 μm to about 3.5 μm diameter, about 1.5 μm to about 3 μm diameter, about 1.5 μm to about 2.5 μm diameter, about 1.5 μm to about 2 μm diameter, about 2 μm to about 5.5 μm diameter, about 2 μm to about 5 μm diameter, about 2 μm to about 4.5 μm diameter, about 2 μm to about 4 μm diameter, about 2 μm to about 3.5 μm diameter, about 2 μm to about 3 μm diameter, or about 2 μm to about 2.5 μm diameter.

In certain embodiments, the particles of the disclosure have a specific surface area (SSA) of at least 3 $m^2/g$, e.g., in the range of 3 $m^2/g$ to 30 $m^2/g$, as measured by the Brunauer-Emmett-Teller (BET) method. The BET specific surface area test procedure is a compendial method included in both the United States Pharmaceopeia and the European Pharmaceopeia. In certain embodiments, the particles have a SSA of at least 4 $m^2/g$, or at least 5 $m^2/g$, or at least 6 $m^2/g$, or even at least 7 $m^2/g$, as measured by BET method. In certain embodiments, the particles have a SSA in the range of 3 $m^2/g$ to 30 $m^2/g$, or 3 $m^2/g$ to 20 $m^2/g$, or 3 $m^2/g$ to 15 $m^2/g$, or 5 $m^2/g$ to 30 $m^2/g$, or 5 $m^2/g$ to 20 $m^2/g$, or 5 $m^2/g$ to 15 $m^2/g$, or 7 $m^2/g$ to 30 $m^2/g$, or 7 $m^2/g$ to 20 $m^2/g$, or 7 $m^2/g$ to 15 $m^2/g$, or even in the range of 7.68 $m^2/g$ to 14.3 $m^2/g$.

The particles can include both agglomerated particles and non-agglomerated particles; because the SSA is determined on a per gram basis it takes into account both agglomerated and non-agglomerated particles in the composition.

In certain embodiments of all aspects disclosed herein, the particles are uncoated (neat) particles; the particles are not covalently bound to any substance; no substances are absorbed or adsorbed onto the surface of the particles; the particles are not encapsulated in any substance; the particles are not coated with any substance; the particles are not microemulsions, nanoemulsions, microspheres, or liposomes of a compound; and/or the particles are not bound to, attached to, encapsulated in, or coated with a monomer, a polymer (or biocompatible polymer), a protein, a surfactant, liposome, or albumin. In some embodiments, a monomer, a polymer (or biocompatible polymer), a copolymer, a protein, a surfactant, or albumin is not absorbed or adsorbed onto the surface of the particles.

Another aspect of the disclosure provides compositions including the ciprofloxacin polymorph of the disclosure as described herein. For example, in certain embodiments of the disclosure, the composition includes particles that comprise the ciprofloxacin polymorph of the disclosure. In certain embodiments, the composition may further include ciprofloxacin particles of Form B. In certain embodiments, the composition may further include ciprofloxacin hydrochloride particles (e.g., ciprofloxacin hydrochloride particles obtained in Example 1).

Another aspect of the disclosure provides pharmaceutical compositions including the ciprofloxacin polymorph of the disclosure as described herein or the particles as described herein, and one or more pharmaceutically acceptable carriers.

In certain embodiments, the compositions of the disclosure and/or the pharmaceutical compositions of the disclosure include a dosage form of ciprofloxacin in a range of 0.1 mg/g to about 100 mg/g. For example, in certain embodiments, the dosage form of ciprofloxacin may be in a range of 0.5 mg/g to about 100 mg/g, about 1 mg/g and about 100 mg/g, about 2 mg/g and about 100 mg/g, about 5 mg/g and about 100 mg/g, about 10 mg/g and about 100 mg/g, about 25 mg/g and about 100 mg/g, about 0.1 mg/g and about 75 mg/g, about 0.5 mg/g and about 75 mg/g, about 1 mg/g and about 75 mg/g, about 2 mg/g and about 75 mg/g, about 5 mg/g and about 75 mg/g, about 10 mg/g and about 75 mg/g, about 25 mg/g and about 75 mg/m, about 0.1 mg/g and about 50 mg/g, about 0.5 mg/g and about 50 mg/g, about 1 mg/g and about 50 mg/g, about 2 mg/g and about 50 mg/g, about 5 mg/g and about 50 mg/g, about 10 mg/g and about 50 mg/g, about 25 mg/g and about 50 mg/m, about 0.1 mg/g and about 25 mg/g, about 0.5 mg/g and about 25 mg/g, about 1 mg/g and about 40 mg/g, about 1 mg/g and about 25 mg/g, about 2 mg/g and about 25 mg/g, about 5 mg/g and about 25 mg/g, about 10 mg/g and about 25 mg/g, about 0.1 mg/g and about 15 mg/g, about 0.5 mg/g and about 15 mg/g, about 1 mg/g and about 15 mg/g, about 2 mg/g and about 15 mg/g, about 5 mg/g and about 15 mg/g, about 10 mg/g and about 15 mg/g, about 0.1 mg/g and about 10 mg/g, about 0.5 mg/g and about 10 mg/g, about 1 mg/g and about 10 mg/g, about 2 mg/g and about 10 mg/g, about 5 mg/g and about 10 mg/g, about 0.1 mg/g and about 5 mg/g, about 0.5 mg/g and about 5 mg/g, about 1 mg/g and about 5 mg/g, about 2 mg/g and about 5 mg/g, about 0.1 mg/g and about 2 mg/g, about 0.5 mg/g and about 2 mg/g, about 1 mg/g and about 2 mg/g, about 0.1 mg/g and about 1 mg/g, about 0.5 mg/g and about 1 mg/g, about 0.1 mg/g and about 0.5 mg/g, about 0.1 mg/g and about 15 mg/g, about 0.5 mg/g and about 15 mg/g, about 1 mg/g and about 15 mg/g, about 2 mg/g and about 15 mg/g, about 5 mg/g and about 15 mg/g, about 3 mg/g and about 8 mg/g, or about 4 mg/g and about 6 mg/g; or at least about 0.1, 0.5, 1, 10, 20, 25, 50, 75, or 100 mg/g ciprofloxacin.

In certain embodiments, the compositions of particles as described herein may be in a form of dry powder compositions, i.e., delivered using any suitable dry powder inhaler (DPI), which is an inhaler device that utilizes the patient's inhaled breath as a vehicle to transport the dry powder drug to the lungs. Dry powders may also comprise one or more carriers, such as lactose, glucose, mannitol, maltitol, maltose, sorbitol, erythritol, trehalose, raffinose, cyclodextrins, dextrose, xylitol, magnesium stearate, distearyl phosphatidylcholine (DSPC), fumaryl diketopiperazine (FDKP), hydroxyapatite, glycine, and any hydrates thereof and/or any combination thereof. Dry powders may also be delivered using a pressurized, metered dose inhaler (MDI), e.g., the Ventolin® metered dose inhaler. Thus, the compositions of the disclosure may contain a solution or suspension of the particle in a pharmaceutically inert liquid propellant, e.g., a chlorofluorocarbon or a hydrofluoroalkane (HFA).

In one embodiment of all aspects of the present disclosure, the particles are present in a liquid carrier, for example, prior to aerosolization. Any suitable liquid carrier may be used, such as an aqueous liquid carrier. Any suitable aqueous liquid carrier can be used, including but not limited to 0.9% saline solution (normal saline) such as 0.9% Sodium Chloride for Injection USP.

In another embodiment of all aspects of the present disclosure, the particles are present in a suspension, for example, prior to aerosolization. In some embodiments, the suspension includes an aqueous carrier. The carrier can comprise buffering agent, osmotic salt and/or surfactant in water, and other agents for adjustment of pH, isotonicity and viscosity.

In some embodiments of all aspects of the present disclosure, the suspension can comprise water and optionally one or more excipients selected from the group consisting of buffer, tonicity adjusting agent, preservative, demulcent, viscosity modifier, osmotic agent, surfactant, antioxidant, alkalinizing agent, acidifying agent, antifoaming agent, and colorant. For example, the suspension can comprise particles, water, buffer and salt. It optionally further comprises a surfactant. In some embodiments, the suspension consists essentially of or consists of water, particles suspended in the water and buffer. The suspension can further contain an osmotic salt.

The suspension can comprise one or more tonicity adjusting agents. Suitable tonicity adjusting agents include by way of example and without limitation, one or more inorganic salts, electrolytes, sodium chloride, potassium chloride, sodium phosphate, potassium phosphate, sodium, potassium sulfates, sodium and potassium bicarbonates and alkaline earth metal salts, such as alkaline earth metal inorganic salts, e.g., calcium salts, and magnesium salts, mannitol, dextrose, glycerin, propylene glycol, and mixtures thereof.

The suspension can comprise one or more buffering agents. Suitable buffering agents include by way of example and without limitation, dibasic sodium phosphate, monobasic sodium phosphate, citric acid, sodium citrate hydrochloric acid, sodium hydroxide, tris(hydroxymethyl)aminomethane, bis(2-hydroxyethyl)iminotris-(hydroxymethyl) methane, and sodium hydrogen carbonate and others known to those of ordinary skill in the art. Buffers are commonly used to adjust the pH to a desirable range for intraperitoneal use. Usually a pH of around 5 to 9, 5 to 8, 6 to 7.4, 6.5 to 7.5, or 6.9 to 7.4 is desired.

The suspension can comprise one or more demulcents. A demulcent is an agent that forms a soothing film over a mucous membrane, such as the membranes lining the peritoneum and organs therein. A demulcent may relieve minor pain and inflammation and is sometimes referred to as a mucoprotective agent. Suitable demulcents include cellulose derivatives ranging from about 0.2 to about 2.5% such as carboxymethylcellulose sodium, hydroxyethyl cellulose, hydroxypropyl methylcellulose, and methylcellulose; gelatin at about 0.01%; polyols in about 0.05 to about 1%, also including about 0.05 to about 1%, such as glycerin, polyethylene glycol 300, polyethylene glycol 400, and propylene glycol; polyvinyl alcohol from about 0.1 to about 4%; povidone from about 0.1 to about 2%; and dextran 70 from about 0.1% when used with another polymeric demulcent described herein.

The suspension can comprise one or more alkalinizing agents to adjust the pH. As used herein, the term "alkalizing agent" is intended to mean a compound used to provide an alkaline medium. Such compounds include, by way of example and without limitation, ammonia solution, ammonium carbonate, potassium hydroxide, sodium carbonate, sodium bicarbonate, and sodium hydroxide and others known to those of ordinary skill in the art.

The suspension can comprise one or more acidifying agents to adjust the pH. As used herein, the term "acidifying agent" is intended to mean a compound used to provide an acidic medium. Such compounds include, by way of example and without limitation, acetic acid, amino acid, citric acid, nitric acid, fumaric acid and other alpha hydroxy acids, hydrochloric acid, ascorbic acid, and nitric acid and others known to those of ordinary skill in the art.

The suspension can comprise one or more viscosity modifiers that increase or decrease the viscosity of the suspension. Suitable viscosity modifiers include methylcellulose, hydroxypropyl methycellulose, mannitol and polyvinylpyrrolidone.

In some embodiments, the compositions and/or pharmaceutical compositions of the disclosure are free of/do not include or contain a polymer/copolymer or biocompatible polymer/copolymer. In some embodiments, the compositions and/or pharmaceutical compositions of the disclosure are free of/do not include or contain a protein. In some embodiments of the disclosure, the compositions and/or pharmaceutical compositions of the disclosure are free of/do not include or contain albumin. In some embodiments of the disclosure, the compositions and/or pharmaceutical compositions of the disclosure are free of/do not include or contain hyaluronic acid. In some embodiments of the disclosure, the compositions and/or pharmaceutical compositions of the disclosure are free of/do not include or contain a conjugate of hyaluronic acid and a therapeutic. In some embodiments of the disclosure, the compositions and/or pharmaceutical compositions of the disclosure are free of/do not include or contain a conjugate of hyaluronic acid and therapeutic. In some aspects of the disclosure, the compositions and/or pharmaceutical compositions of the disclosure are free of/do not include or contain poloxamers, polyanions, polycations, modified polyanions, modified polycations, chitosan, chitosan derivatives, metal ions, nanovectors, poly-gamma-glutamic acid (PGA), polyacrylic acid (PAA), alginic acid (ALG), vitamin E-TPGS, dimethyl isosorbide (DMI), methoxy PEG 350, citric acid, anti-VEGF antibody, ethylcellulose, polystyrene, polyanhydrides, polyhydroxy acids, polyphosphazenes, polyorthoesters, polyesters, polyamides, polysaccharides, polyproteins, styrene-isobutylene-styrene (SIBS), a polyanhydride copolymer, polycaprolactone, polyethylene glycol (PEG), poly (bis(P-carboxyphenoxy)propane-sebacic acid, poly(d,l-lactic acid) (PLA), poly(d.l-lactic acid-co-glycolic acid) (PLAGA), and/or poly(D, L lactic-co-glycolic acid (PLGA).

Methods of Treatment

Another aspect of the disclosure provides methods for treating a bacterial infection. Such methods include administering to a subject in need thereof the polymorph of the disclosure as described herein, or the polymorph particles as described herein, or the composition of the disclosure as described herein, or the pharmaceutical composition of the disclosure as described herein (collectively referred to as "therapeutics'), in an amount efficient to treat the infection.

The subject may be any mammal subject, including but not limited to humans and other primates, dogs, cats, horses, cattle, pigs, sheep, goats, etc.

The "amount effective" of the therapeutic of all aspects of the disclosure can be determined by attending medical personnel based on all relevant factors. The therapeutic may be the sole therapeutic administered, or may be administered with other therapeutics as deemed appropriate by attending medical personnel in light of all circumstances.

As used herein in all aspects of the disclosure, the terms "treatment" and "treating" means (i) inhibiting progression of the disorder; (ii) inhibiting the disorder, for example, inhibiting a disorder in an individual who is experiencing or displaying the pathology or symptomatology of the disease, condition or disorder; or (iii) ameliorating the disorder, for example, ameliorating a disorder in an individual who is experiencing or displaying the pathology or symptomatology of the disorder (i.e., reversing or improving the pathology and/or symptomatology) such as decreasing the severity of disorder.

In various non-limiting embodiments, the bacterial infection may include bone infections, joint infections, intra-abdominal infections, diarrhea, respiratory tract infections, pneumonia, skin infections, typhoid fever, urinary tract infections, endocarditis, gastroenteritis, malignant otitis externa, cellulitis, prostatitis, anthrax, and chancroid. In various other non-limiting embodiments, the bacterial infection comprises an infection by *E. coli, Haemophilus influenza, Klebsiella pneumoniae, Legionella pneumophilla, Pseudomonas aeruginosa, Proteus mirabilis, Moraxells catarrhalis, Staphylococcus aureus, Streptococcus pneumoniae, Enterococcus faecalis, Bacillus anthracis,* or *Streptococcus pyogenes*. In certain embodiments of the disclosure, the bacterial infection is respiratory infection.

In the methods of treatment of the disclosure, the therapeutic may be administered by any suitable route, including (but not limited to) orally, sublingually, by injection, or via pulmonary administration (e.g., inhalation or nebulization). In certain embodiments, administration is by pulmonary administration, comprising inhalation of the therapeutic, such as a particle composition, such as by nasal, oral inhalation, or both. In this embodiment, the therapeutic, such as a particle composition, may be formulated as a dry powder or as an aerosol (i.e., liquid droplets of a stable dispersion or suspension of the particles in a gaseous medium). In certain embodiments, the methods comprise inhalation of the therapeutic via a DPI (e.g., therapeutic is formulated as a dry powder composition, with or without carriers). In another embodiment, the methods comprise inhalation of the therapeutic, such as particles aerosolized via a pMDI, wherein therapeutic, such as particles or suspensions thereof are suspended in a suitable propellant system (including but not limited to hydrofluoroalkanes (HFAs) containing at least one liquefied gas in a pressurized container sealed with a metering valve. Actuation of the valve results in delivery of a metered dose of an aerosol spray of the ciprofloxacin particles or suspensions thereof. The therapeutics, such as particle compositions, may also be delivered by aerosol, e.g., may be deposited in the airways by gravitational sedimentation, inertial impaction, and/or diffusion. In one specific embodiment, the methods comprise inhalation of the therapeutics, such as particles, aerosolized via nebulization. In this embodiment, the nebulization provides pulmonary delivery to the subject of dry powder or aerosol droplets of the therapeutic, such as particles or suspension thereof.

Methods of Synthesis

Another aspect of the disclosure provides methods for preparing the polymorph of the disclosure as provided herein. Such methods may include evaporative crystallization, antisolvent crystallization, modified versions of "precipitation with compressed antisolvents" (PCA) methods as disclosed in U.S. Patent Publication Number 2016/0354336, International Patent Publications WO 2016/197091, WO 2016/197100, and WO 2016/197101 (all of which are herein incorporated by reference), or spray drying.

Any suitable solvent and antisolvent may be used. In one non-limiting embodiment, the solvent may comprise hexafluoroisopropanol (1,1,1,3,3,3-hexafluoro-2-propanol or HFIP). In certain embodiments, the antisolvent used in the methods of the disclosure is acetone, methanol, ethanol, isopropyl alcohol, and ethyl acetate. Removal of residual solvent, such as HFIP can be accomplished through extraction, either under super-critical conditions or atmospheric conditions, using a solvent in which the ciprofloxacin has limited or no solubility.

In certain specific embodiment of the disclosure, methods for preparing the polymorph particles of the disclosure as provided herein include:
  (a) obtaining a solution or a suspension of ciprofloxacin in a solvent or mixture of solvents; and
  (b) removing the solvent or mixture of solvents from said solution or suspension to form the polymorph particles.

In a specific embodiment of the disclosure, methods for preparing the polymorph particles of the disclosure as provided herein include:
  (a) obtaining a solution or a suspension of ciprofloxacin in a solvent or mixture of solvents;
  (b) feeding and spraying said solution or suspension into a pressurized chamber to obtain a stream of atomized droplets; and
  (c) removing the solvent or mixture of solvents from said droplets to form the polymorph particles.

In certain such embodiments, said solution or suspension fed and sprayed into the pressurized chamber further comprises a compressed fluid. In certain such embodiments, the method may further comprise (e) receiving the particles through the outlet of the pressurized chamber; and (f) collecting the particles in a collection device.

In one example embodiment of the methods for preparing the polymorph particles of the disclosure as provided herein, the method includes:
  (a) introducing (i) a solution or a suspension of ciprofloxacin into a nozzle inlet, and (ii) a compressed fluid into an inlet of a vessel defining a pressurized chamber;
  (b) passing the solution out of a nozzle orifice and into the pressurized chamber to produce an output stream of atomized droplets, wherein the nozzle orifice is located between 5 mm and 20 mm from a sonic energy source located within the output stream, wherein the sonic energy source produces sonic energy with power output of between about 110 watts (20%) and about 550 watts (80%) during the passing, and wherein the nozzle orifice has a diameter of between 50 µm and 100 µm;
  (c) contacting the atomized droplets with the compressed fluid, to cause depletion of the solvent from the atomized droplets, to produce ciprofloxacin particles,
    wherein (a), (b), and (c) are carried out under supercritical temperature and pressure for the compressed fluid.

In certain embodiments, such method may further comprise (d) contacting the atomized droplets produced in step (c) with an antisolvent to cause further depletion of the solvent from the ciprofloxacin particles, wherein step (d) is carried out under supercritical temperature and pressure for the antisolvent. In a further embodiment, the methods may comprise: (e) receiving the particles through the outlet of the pressurized chamber; and (f) collecting the particles in a collection device.

In a preferred embodiment of the methods for preparing the polymorph particles of the disclosure as provided herein, the solvent is HFIP.

Ciprofloxacin may make up any suitable percentage, by weight of the overall solution. In certain embodiments, the solution or suspension has concentration of ciprofloxacin in the range of 10 mg/mL and 100 mg/mL, or 30 mg/mL and 70 mg/mL, or 40 mg/mL and 60 mg/mL, or 45 mg/mL and 55 mg/mL, or about 50 mg/mL.

In one embodiment, the compressed fluid is super critical carbon dioxide; in another embodiment, the antisolvent is super critical carbon dioxide. In a further embodiment, the method is carried out between 31.1° C. to about 60° C., and at between about 1071 psi and about 1800 psi. In another embodiment, the method is carried out at between about 41° C.-45° C. (e.g., 37.6° C.-38.3° C.). In a further embodiment, the method is carried out at between about 1100 psi and about 1300 psi. In another embodiment, the nozzle orifice is located between 5 mm and 20 mm, or between 5 mm and 15 mm from a sonic energy source located within the output stream, and the sonic energy source produces sonic energy with amplitude between about 20% and about 80% during the passing. In a further embodiment, the sonic probe operates at a frequency of between about 18 kHz and about 22 kHz. In various embodiments, the nozzle orifice diameter is between about 50 and about 100 μm.

In a specific embodiment, the solvent is HFIP, the compressed fluid is super critical carbon dioxide; the antisolvent is super critical carbon dioxide, the method is carried out at between about 41° C.-45° C. (e.g., 37.6° C.-38.3° C.) and at between about 1100 psi and about 1300 psi, and the therapeutic is ciprofloxacin or a pharmaceutically acceptable salt thereof.

In certain embodiments, the antisolvent used in the methods of the disclosure is acetone, methanol, ethanol, isopropyl alcohol, and ethyl acetate.

In all aspects of the disclosure involving methods for producing particles, the methods of the disclosure utilize a sonic energy source located directly in the output stream of the therapeutic dissolved in the solvent, as disclosed in U.S. Patent Publication Number 2016/0354336, incorporated by reference herein in its entirety. Any suitable source of sonic energy may be used that is compatible with the methods of the disclosure, including but not limited to sonic horn, a sonic probe, or a sonic plate. In various embodiments, the nozzle orifice is located between about 2 mm and about 20 mm, about 2 mm and about 18 mm, about 2 mm and about 16 mm, about 2 mm and about 14 mm, about 2 mm and about 12 mm, about 2 mm and about 10 mm, about 2 mm and about 8 mm, about 2 mm and about 6 mm, about 2 mm and about 4 mm, about 4 mm and about 20 mm, about 4 mm and about 18 mm, about 4 mm and about 16 mm, about 4 mm and about 14 mm, about 4 mm and about 12 mm, about 4 mm and about 10 mm, about 4 mm and about 8 mm, about 4 mm and about 6 mm, about 6 mm and about 20 mm, about 6 mm and about 18 mm, about 6 mm and about 16 mm, about 6 mm and about 14 mm, about 6 mm and about 12 mm, about 6 mm and about 10 mm, about 6 mm and about 8 mm, about 8 mm and about 20 mm, about 8 mm and about 18 mm, about 8 mm and about 16 mm, about 8 mm and about 14 mm, about 8 mm and about 12 mm, about 8 mm and about 10 mm, about 10 mm and about 20 mm, about 10 mm and about 18 mm, about 10 mm and about 16 mm, about 10 mm and about 14 mm, about 10 mm and about 12 mm, about 12 mm and about 20 mm, about 12 mm and about 18 mm, about 12 mm and about 16 mm, about 12 mm and about 14 mm, about 14 mm and about 20 mm, about 14 mm and about 18 mm, about 14 mm and about 16 mm, about 16 mm and about 20 mm, about 16 mm and about 18 mm, about 18 mm and about 20 mm, about 2 mm, about 3 mm, about 4 mm, about 5 mm, about 6 mm, about 7 mm, about 8 mm, about 9 mm, about 10 mm, about 11 mm, about 12 mm, about 13 mm, about 14 mm, about 15 mm, about 16 mm, about 17 mm, about 18 mm, about 19 mm, or about 20 mm from the sonic energy source.

Any suitable source of sonic energy may be used that is compatible with the methods of the making the particles of any aspect of the disclosure, including but not limited to sonic horn, a sonic probe, or a sonic plate. In various further embodiments, the sonic energy source produces sonic energy with a power output between about 7 watts and about 700 watts. In light of the teachings herein, one of skill in the art can determine an appropriate sonic energy source having a specific total power output to be used. In one embodiment, the sonic energy source has a total power output of between about 500 and about 900 watts; in various further embodiments, between about 600 and about 800 watts, about 650-750 watts, or about 700 watts.

The power output may also be expressed in terms of percent sonic power, with a conversion to watts as follows: 100.00% is about 550 W; 80.00% is about 440 W; 60.00% is about 330 W; 40.00% is about 220 W; and 20.00% is about 110 W. In certain embodiments, the power output is between 10% and 100% (e.g., 55-550 W), or between 30% and 90% (e.g., 165-495 W), or between 40% and 80% (e.g., 220-440 W), or between 50% and 70% (e.g., 275-385 W), or about 60% (e.g., 330 W).

In various further embodiments all aspects of the disclosure involving methods for producing particles, the sonic energy source produces sonic energy with a power output between about 7 and about 550 watts, about 55 and about 550 watts, about 110 and about 550 watts, about 165 and about 550 watts, about 220 and about 550 watts, about 275 and about 550 watts, about 300 and about 550 watts, about 330 and about 550 watts, about 440 and about 550 watts, about 7 and about 440 watts, about 55 and about 440 watts, about 110 and about 440 watts, about 165 and about 440 watts, about 220 and about 440 watts, about 275 and about 440 watts, about 300 and about 440 watts, about 330 and about 440 watts, about 7 and about 385 watts, about 55 and about 385 watts, about 110 and about 385 watts, about 165 and about 385 watts, about 220 and about 385 watts, about 275 and about 385 watts, about 300 and about 385 watts, about 330 and about 385 watts, about 7 and about 280 watts, about 35 and about 280 watts, about 70 and about 280 watts, about 140 and about 280 watts, about 210 and about 280 watts, about 7 and about 210 watts, about 35 and about 210 watts, about 70 and about 210 watts, about 140 and about 210 watts, about 7 and about 140 watts, about 35 and about 140 watts, about 70 and about 140 watts, about 5, 28, 50, 110, 165, 220, 275, 330, 385, 440, 495, or about 550 watts. In various embodiments, the sonic energy source produces sonic energy with power output of about 1%-80%, 20-80%, 30-70%, 40-60%, or about 60% of the total power that can be generated using the sonic energy source. In light of the teachings herein, one of skill in the art can determine an appropriate frequency to be utilized on the sonic energy source. In one embodiment, a frequency of between about 18 and about 22 kHz on the sonic energy source is utilized. In various other embodiments, a frequency of between about 19 and about 21 kHz, about 19.5 and about 20.5, or a frequency of about 20 kHz on the sonic energy source is utilized.

In various further embodiments all aspects of the disclosure involving methods for producing particles, the nozzle orifice has a diameter of between about 20 µm and about 125 µm, about 20 µm and about 115 µm, about 20 µm and about 100 µm, about 20 µm and about 90 µm, about 20 µm and about 80 µm, about 20 µm and about 70 µm, about 20 µm and about 60 µm, about 20 µm and about 50 µm, about 20 µm and about 40 µm, about 20 µm and about 30 µm, between about 30 µm and about 125 µm, about 30 µm and about 115 µm, about 30 µm and about 100 µm, about 30 µm and about 90 µm, about 30 µm and about 80 µm, about 30 µm and about 70 µm, about 30 µm and about 60 µm, about 30 µm and about 50 µm, about 30 µm and about 40 µm, between about 40 µm and about 125 µm, about 40 µm and about 115 µm, about 40 µm and about 100 µm, about 40 µm and about 90 µm, about 40 µm and about 80 µm, about 40 µm and about 70 µm, about 40 µm and about 60 µm, about 40 µm and about 50 µm, between about 50 µm and about 125 µm, about 50 µm and about 115 µm, about 50 µm and about 100 µm, about 50 µm and about 90 µm, about 50 µm and about 80 µm, about 50 µm and about 70 µm, about 50 µm and about 60 µm, between about 60 µm and about 125 µm, about 60 µm and about 115 µm, about 60 µm and about 100 µm, about 60 µm and about 90 µm, about 60 µm and about 80 µm, about 60 µm and about 70 µm, between about 70 µm and about 125 µm, about 70 µm and about 115 µm, about 70 µm and about 100 µm, about 70 µm and about 90 µm, about 70 µm and about 80 µm, between about 80 µm and about 125 µm, about 80 µm and about 115 µm, about 80 µm and about 100 µm, about 80 µm and about 90 µm, between about 90 µm and about 125 µm, about 90 µm and about 115 µm, about 90 µm and about 100 µm, between about 100 µm and about 125 µm, about 100 µm and about 115 µm, between about 115 µm and about 125 µm, about 20 µm, 30 µm, 40 µm, 50 µm, 60 µm, 70 µm, 80 µm, 90 µm, 100 µm, 115 µm, or about 120 µm. The nozzle is inert to both the solvent and the compressed fluid used in the methods.

In another embodiment all aspects of the disclosure involving methods for producing particles, the nozzle may include an outlet aperture that may include a plurality of ridges to create a vortex within the nozzle such that the solvent exits the nozzle via turbulent flow. In one embodiment, the nozzle may include a porous frit interior to the nozzle such that the solvent exits the nozzle via turbulent flow. In another embodiment, the outlet aperture of the nozzle may have a small diameter such that the solvent exits the nozzle via turbulent flow. These various embodiments that cause turbulent flow may assist in mixing the solvent with the antisolvent within the pressurized chamber. Further, the inlet tube of the nozzle may have an inner diameter with a range from about 1.5875 mm to about 6.35 mm.

In further examples all aspects of the disclosure involving methods for producing particles, the system may include a plurality of nozzles, with each nozzle positioned at a different angle between a longitudinal axis of the vessel and a longitudinal axis of the nozzle and/or a different distance between the nozzle orifice and the sonic energy source. A given nozzle of the plurality of nozzles may be chosen for a given production run to produce a certain type of a particle having a given d10, d50, d90, and/or SSA.

The compressed fluid for use in all aspects of the disclosure involving methods for producing particles is capable of forming a supercritical fluid under the conditions used, and the therapeutic that forms the particles is poorly soluble or insoluble in the compressed fluid. As is known to those of skill in the art, a supercritical fluid is any substance at a temperature and pressure above its critical point, where distinct liquid and gas phases do not exist. Feeding and spraying in (b) of the methods for making particles of the disclosure are carried out under supercritical temperature and pressure for the compressed fluid, such that the compressed fluid is present as a supercritical fluid during these processing steps.

The compressed fluid can serve as a solvent for and can be used to remove unwanted components in the particles. Any suitable compressed fluid may be used in the methods of the disclosure; exemplary such compressed fluids are disclosed in U.S. Pat. Nos. 5,833,891 and 5,874,029. In one non-limiting embodiment, suitable supercritical fluid-forming compressed fluids and/or antisolvents can comprise carbon dioxide, ethane, propane, butane, isobutane, nitrous oxide, xenon, sulfur hexafluoride and tnfluoromethane. The antisolvent causes further solvent depletion, is a compressed fluid as defined above, and may be the same compressed fluid, or may be different. In one embodiment, the antisolvent of is the same as the compressed fluid. In a preferred embodiment, the compressed fluid and the antisolvent are both super-critical carbon dioxide. In all cases, the compressed fluid and antisolvent should be substantially miscible with the solvent while the therapeutic should be substantially insoluble in the compressed fluid, i.e., the therapeutic, at the selected solvent/compressed fluid contacting conditions, should be no more than about 10% by weight soluble in the compressed fluid or antisolvent, and preferably no more than 9%, 8%, 7%, 6%, 5%, 4%, 3%, 2%, 1%, 0.5%, soluble, or essentially completely insoluble. In one preferred embodiment, the compressed fluid and the antisolvent are the same.

The supercritical conditions used in the methods for making particles of all aspects of the disclosure are typically in the range of from 1× to about 1.4×, or 1× to about 1.2× of the critical temperature of the supercritical fluid (so long as the therapeutic is thermally stable at the elevated temperature), and from 1× to about 7×, or 1× to about 2×, of the of the supercritical pressure for the compressed fluid. It is well within the level of those of skill in the art to determine the critical temperature and pressure for a given compressed fluid or antisolvent. In one embodiment, the compressed fluid and antisolvent are both super critical carbon dioxide, and the critical temperature is at least 31.1° C. and up to about 60° C., and the critical pressure is at least 1071 psi and up to about 1800 psi or higher (i.e.: no theoretical upper limit, so long as the processing equipment can sustain the higher psi). In another embodiment, the compressed fluid and antisolvent are both super critical carbon dioxide, and the critical temperature is at least 35° C. and up to about 55° C. or higher (i.e.: no theoretical upper limit, so long as the processing equipment can sustain the higher temperature), and the critical pressure is at least 1070 psi and up to about 1500 psi. It will be understood by those of skill in the art that the specific critical temperature and pressure may be different at different steps during the processing. For example, $CO_2$ is super critical at all pressures greater than 1071 psi if the temperature is above 31.1° C.

In certain embodiments, the temperature and pressure of the pressurized chamber is a supercritical temperature and pressure for the compressed fluid; e.g., the temperature of the pressurized chamber is in the range of 30° C. to 60° C., or 30° C. to 50° C., or 30° C. to 40° C., or 30° C. to 35° C., or about 35° C.; and e.g., the pressure of the pressurized chamber is in the range of 1000 psi to 1800 psi, or 1000 psi to 1600 psi, or 1000 psi to 1400 psi, or 1000 psi to 1200 psi, or 1200 psi to 1800 psi, or 1200 psi to 1600 psi, or 1200 psi to 1400 psi, or about 1200 psi.

Any suitable pressurized chamber may be used, including but not limited to those disclosed in U.S. Pat. Nos. 5,833,891 and 5,874,029. Similarly, the steps of contacting the atomized droplets with the compressed fluid to cause depletion of the solvent from the droplets; and contacting the droplets with an antisolvent to cause further depletion of the solvent from the droplets, to produce particles can be carried out under any suitable conditions, including but not limited to those disclosed in U.S. Pat. Nos. 5,833,891 and 5,874,029.

The flow rate can be adjusted as high as possible to optimize output but below the pressure limitations for the equipment, including the nozzle orifice. In one embodiment, the flow rate of the solution through the nozzle has a range from about 0.5 mL/min to about 30 mL/min. In various further embodiments, the flow rate is between about 0.5 mL/min to about 25 mL/min, 0.5 mL/min to about 20 mL/min, 0.5 mL/min to about 15 mL/min, 0.5 mL/min to about 10 mL/min, 0.5 mL/min to about 4.5 mL/min, about 1 mL/min to about 30 mL/min, about 1 mL/min to about 25 mL/min, about 1 mL/min to about 20 mL/min, 1 mL/min to about 15 mL/min, about 1 mL/min to about 10 mL/min, about 2 mL/min to about 30 mL/min, about 2 mL/min to about 25 mL/min, about 2 mL/min to about 20 mL/min, about 2 mL/min to about 15 mL/min, or about 2 mL/min to about 10 mL/min. The solution of therapeutic subject to the flow rate can be any suitable concentration, such as between about 1 mg/ml and about 80 mg/ml.

In one embodiment, the methods further comprise receiving the plurality of particles through the outlet of the pressurized chamber; and collecting the plurality of particles in a collection device.

Another aspect of the disclosure provides a polymorph prepared by the methods of the disclosure as provided herein.

Certain aspects of the disclosure are illustrated further by the following examples, which are not to be construed as limiting the disclosure in scope or spirit to the specific procedures and compounds described in them.

EXAMPLES

Materials and Methods

Particle Size Analysis

Suspensions of the ciprofloxacin were prepared in n-hexane containing 0.1% lecithin. The suspensions were sonicated in a bath or with a sonic probe prior to analysis to deagglomerate and form a homogeneous suspension. Particle size was analyzed by both light obscuration and laser diffraction methods. A Particle Sizing Systems AccuSizer 780 SIS system was used for the light obscuration method, and Malvern Mastersizer 3000 Particle Analyzer or Shimadzu SALD-7101 was used for the laser diffraction method.

Specific Surface Area Analysis

Specific Surface Area (SSA) was measured by the Brunauer-Emmett-Teller (BET) method. In short, the testing sample was mounted to a Porous Materials Inc. SORPTOMETER®, model BET-202A. The automated test was then carried out using the BETWIN® software package and the surface area of each sample was subsequently calculated.

Dissolution Studies

Approximately 10 mg of material were added directly to the dissolution bath containing water at 37° C., and a USP Apparatus II (Paddle), operating at 50 rpm. At 2, 5, 10, 20, 30, 60, and 120 minutes, a 5 mL aliquot was removed, filtered through a 0.22 μm filter and analyzed on a U(V/V) is spectrophotometer at 270 nm. Absorbance values of the samples were compared to those of standard solutions prepared in dissolution media to determine the amount of material dissolved.

X-Ray Powder Diffraction

X-Ray Powder Diffraction (XRPD) data was obtained by standard techniques using Seimens D5000 diffractometer operating with a Cu Kα radiation source at 40 kW, 35 mA. The scanning parameters ranged from 5 to 50° 2θ (±0.02°) and a continuous scan at a rate of about 2° 2θ/minute.

Infrared Spectroscopy

Fourier-transform infrared spectroscopy (FTIR) spectral data was obtained by standard techniques using Shimadzu MIRacle 10 FTIR spectrometer in attenuated total reflectance (ATR) mode. Samples were scanned between 600 and 4000 $cm^{-1}$. A total of 32 scans were made with a resolution of 4 $cm^{-1}$.

Differential Scanning Calorimetery

Differential scanning calorimetery (DSC) was performed using an Shimadzu DSC-60. Samples were analyzed using a temperature program from 30 to 300° C. at a rate of 10° C./minute.

Example 1

Ciprofloxacin hydrochloride (1-cyclopropyl-6-fluoro-4-oxo-7-(piperazin-1-yl)-1,4-dihydroquinoline-3-carboxylic acid hydrochloride salt) particles were prepared based on methods and systems as disclosed herein and in U.S. Patent Publication Number 2016/0354336, incorporated by reference in its entirety.

In short, a drug solution of ciprofloxacin hydrochloride in hexafluoroisopropanol (1,1,1,3,3,3-hexafluoro-2-propanol or HFIP) having a concentration of 40 mg/mL was prepared. The drug solution was placed in a container attached to a drug solution inlet on the crystallization chamber. The chamber heated to 38° C. and pressurized to 1200 psi was charged with supercritical $CO_2$ at a flowrate of 65 slpm. Sonication was initialized and maintained at 20% (140 W), or 40% (280 W), or 60% (420 W), or 80% (560 W) unit amplitude depending on the experiment (and as shown in FIG. 3A). Once the desired system pressure, temperature, and $CO_2$ flowrate were reached and remained steady, the drug solution was introduced into the system vessel at flowrate of 2 mL/min using Lennox nozzle. Several Lennox nozzle diameters (e.g., between 50 μm and 100 μm) and nozzle positions (between 5 mm and 20 mm from the sonic probe) were examined depending on the experiment as shown in FIG. 3B, 3C. Drug crystallization occurred in the vessel and during this period the system pressure, temperature, and flow rate were kept constant. Once desired amount of drug solution has been introduced into the system, the solution inlet valve was closed and pure solvent (3-5 mL) was introduced through the nozzle in order to rinse the nozzle. Supercritical $CO_2$ was continually pumped through the system for about 30 minutes to flush all remaining solvent and dry the system. The sonication was then stopped, and the drug particles were collected from the system vessel and oven dried for 20 hours to remove all residual solvent.

The particle size distribution of the raw ciprofloxacin hydrochloride material and the ciprofloxacin hydrochloride processed by this method is provided in FIG. 2. The smaller particle size of the processed ciprofloxacin hydrochloride is also evident from electron micrographs in FIG. 1, which shows raw material (FIG. 1A, 50 μm scale) and processed material (FIG. 1B, 5 μm scale).

The example properties of processed ciprofloxacin hydrochloride particles, as compared to the raw ciprofloxacin hydrochloride, are shown in Table 1. The processed particles were obtained using the sonication at 80% (560 W), nozzle a diameter of 50 μm and positioned 15 mm from the sonic probe

TABLE 1

| | Ciprofloxacin hydrochloride | | |
|---|---|---|---|
| Particle properties | Raw material | Example 1 processed | % Change |
| d10 (μm) | 6.05 | 0.61 | −90 |
| d50 (μm) | 22.7 | 1.37 | −94 |
| d90 (μm) | 56.0 | 3.64 | −94 |
| SSA (m$^2$/g) | 7.68 | 19.42 | +153 |

Example 2

Ciprofloxacin (1-cyclopropyl-6-fluoro-4-oxo-7-(piperazin-1-yl)-1,4-dihydroquinoline-3-carboxylic acid; or ciprofloxacin free base) particles were also prepared based on methods and systems as disclosed herein and in U.S. Patent Publication Number 2016/0354336. For example, a drug solution of ciprofloxacin in HFIP having a concentration of 50 mg/mL was prepared. The drug solution was placed in a container attached to a drug solution inlet on the crystallization chamber. The chamber heated to 35° C. and pressurized to 1200 psi was charged with supercritical $CO_2$ at a flowrate of 70 slpm. Sonication was initialized and maintained at 60% unit amplitude (about 330 W). During sonication, a sonic deflector was used. Once the desired system pressure, temperature, and $CO_2$ flowrate were reached and remained steady, the drug solution was introduced into the system vessel at flowrate of 2 mL/min using Lennox nozzle having a diameter of 50 μm and positioned 8 mm from the sonic probe. Drug crystallization occurred in the vessel and during this period the system pressure, temperature, and flow rate were kept constant. Once desired amount of drug solution has been introduced into the system, the solution inlet valve was closed and pure solvent (3-5 mL) was introduced through the nozzle in order to rinse the nozzle. Supercritical $CO_2$ was continually pumped through the system for about 30 minutes to flush all remaining solvent and dry the system. The sonication was then stopped, and the drug particles were collected from the system vessel and oven dried (about 120° C.) for 20 hours to remove all residual solvent.

Differences between the conventional polymorph (i.e., unprocessed, raw ciprofloxacin, or Form B) and the new polymorph obtained by the process (i.e., processed ciprofloxacin, or Form A) were confirmed both XRPD and FTIR as noted below.

Figure 4:
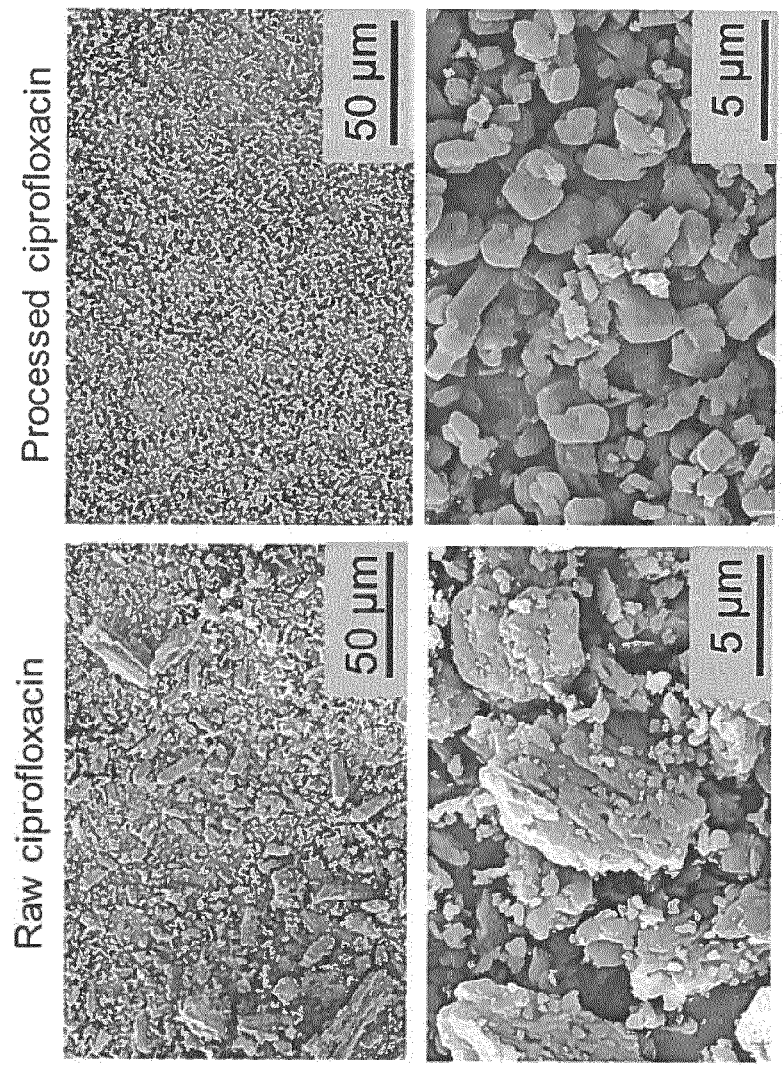
FIG. 4 provides electron micrograph of ciprofloxacin particles. Left panels shows raw material unprocessed by any methods of the disclosure; and the right panels show the processed particles (batch 3) obtained using the method provided in Example 2.

The properties of ciprofloxacin processed by this method are provided in Table 2. The smaller particle size of the processed ciprofloxacin is also evident from electron micrographs in FIG. 4 that compares the raw material and the processed material (batch 3).

TABLE 2

| | Ciprofloxacin | | | |
|---|---|---|---|---|
| | | Example 2 processed | | |
| Particle properties | Raw material | Batch 1 | Batch 2 | Batch 3 |
| d10 (μm) | 1.44 | 1.62 | 1.79 | 1.19 |
| d50 (μm) | 14.8 | 4.63 | 5.57 | 3.26 |
| d90 (μm) | 244 | 9.32 | 13.3 | 6.65 |
| SSA (m$^2$/g) | 11.8 | 7.68 | 14.3 | 12.9 |
| m.p. (DSC) (° C.) | 263.50 | 265.04 | 270.00 | 266.22 |

Figure 5A:
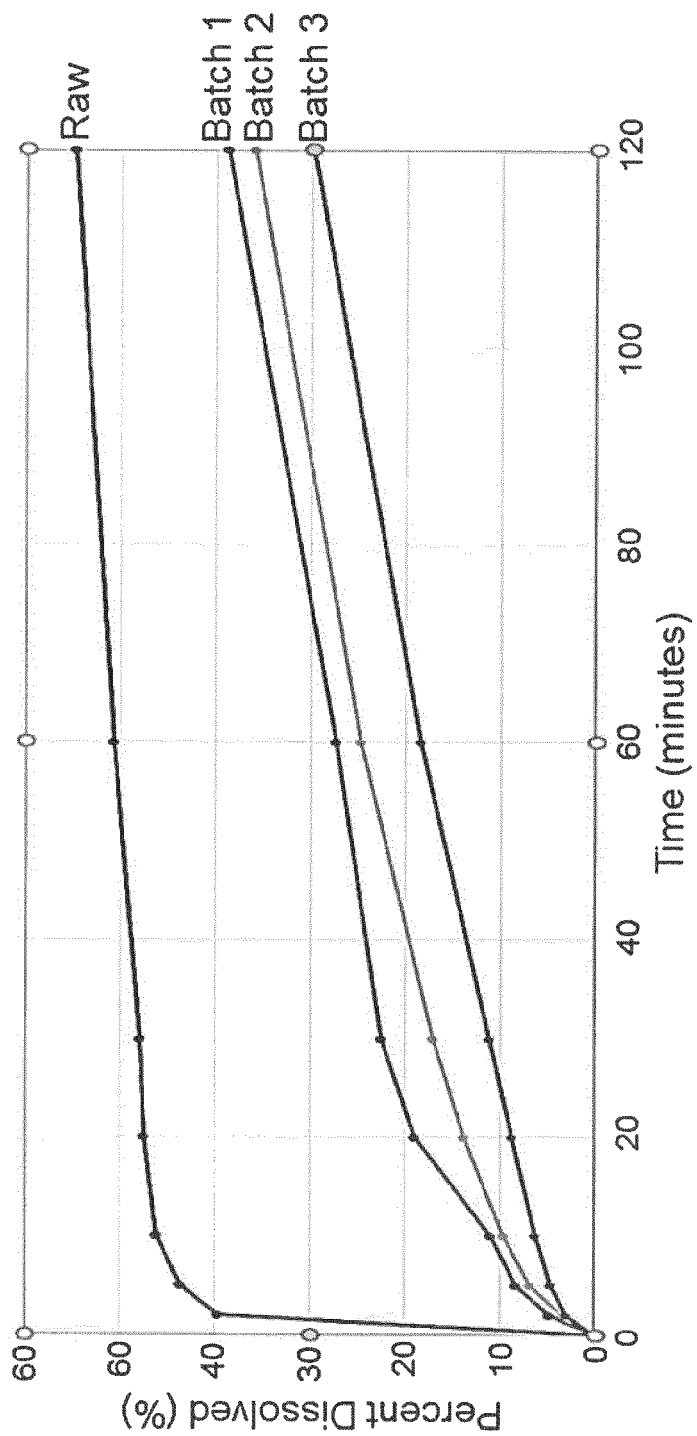
FIG. 5 illustrates the dissolution rates of ciprofloxacin particles in purified water. (A) compares unprocessed, raw ciprofloxacin (labeled Raw) with batches 1-3 of the processed ciprofloxacin particles obtained using the method provided in Example 2. (B) compares unprocessed, raw ciprofloxacin and unprocessed, raw ciprofloxacin hydrochloride (labeled Raw HCl salt) with batch 3 of the processed ciprofloxacin particles obtained using the method provided in Example 2.
Figure 5B:
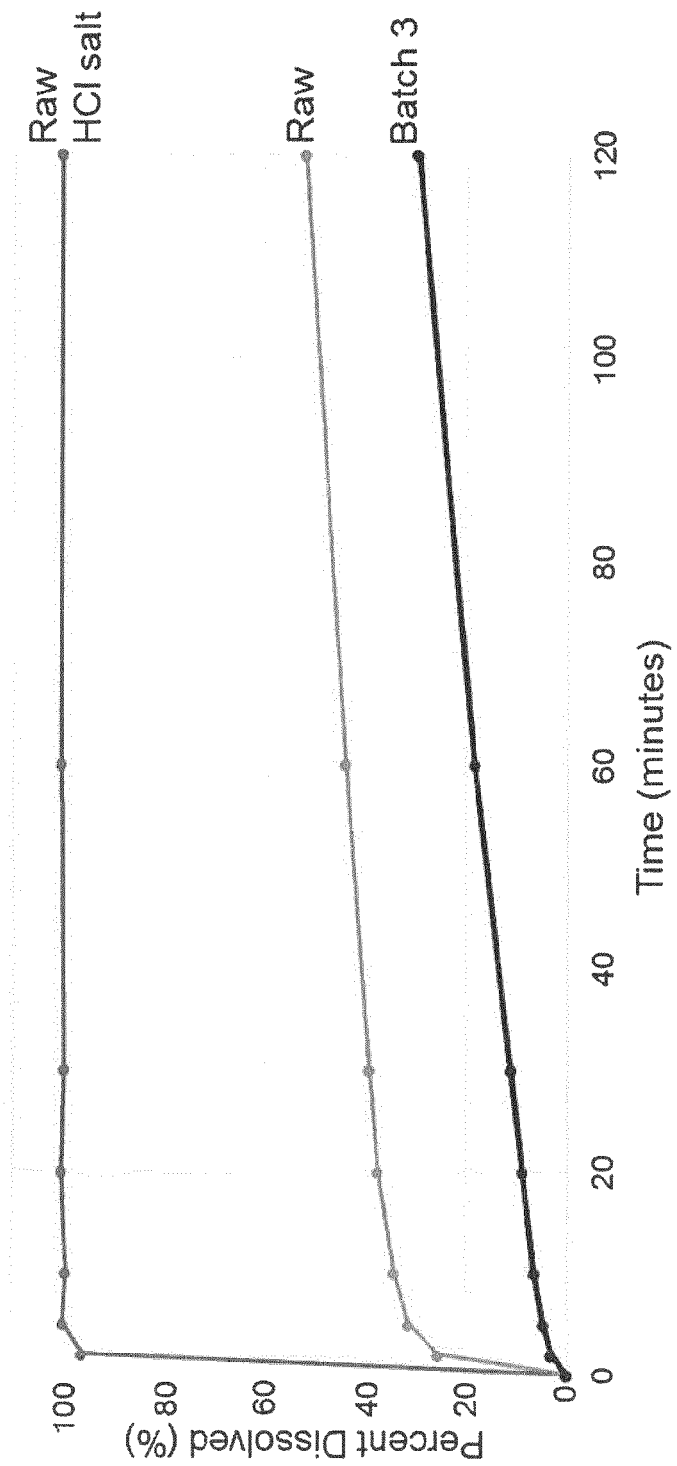

The dissolution rates (carried out as provided above) of the processed ciprofloxacin particles produced by this method and the raw material are provided in Table 3 and graph in FIG. 5A. In addition, as illustrated in FIG. 5B, the processed ciprofloxacin of Example 2 also showed a significantly slower rate of dissolution in water than unprocessed, raw ciprofloxacin (e.g., ca. 2× at 60 minutes).

TABLE 3

| | Dissolution of ciprofloxacin (% dissolved) | | | |
|---|---|---|---|---|
| | | Example 2 processed | | |
| Time (minute) | Raw material | Batch 1 | Batch 2 | Batch 3 |
| 0 | 0.0 | 0.0 | 0.0 | 0.0 |
| 2 | 25.5 | 4.8 | 3.5 | 3.0 |
| 5 | 31.3 | 8.3 | 6.8 | 4.6 |
| 10 | 34.4 | 11.0 | 9.6 | 6.3 |
| 20 | 37.6 | 18.9 | 13.7 | 8.7 |
| 30 | 39.3 | 22.5 | 17.0 | 11.1 |
| 60 | 44.1 | 27.3 | 24.7 | 18.4 |
| 120 | 52.2 | 38.9 | 36.1 | 29.9 |

Characterization by XRPD

Figure 6:
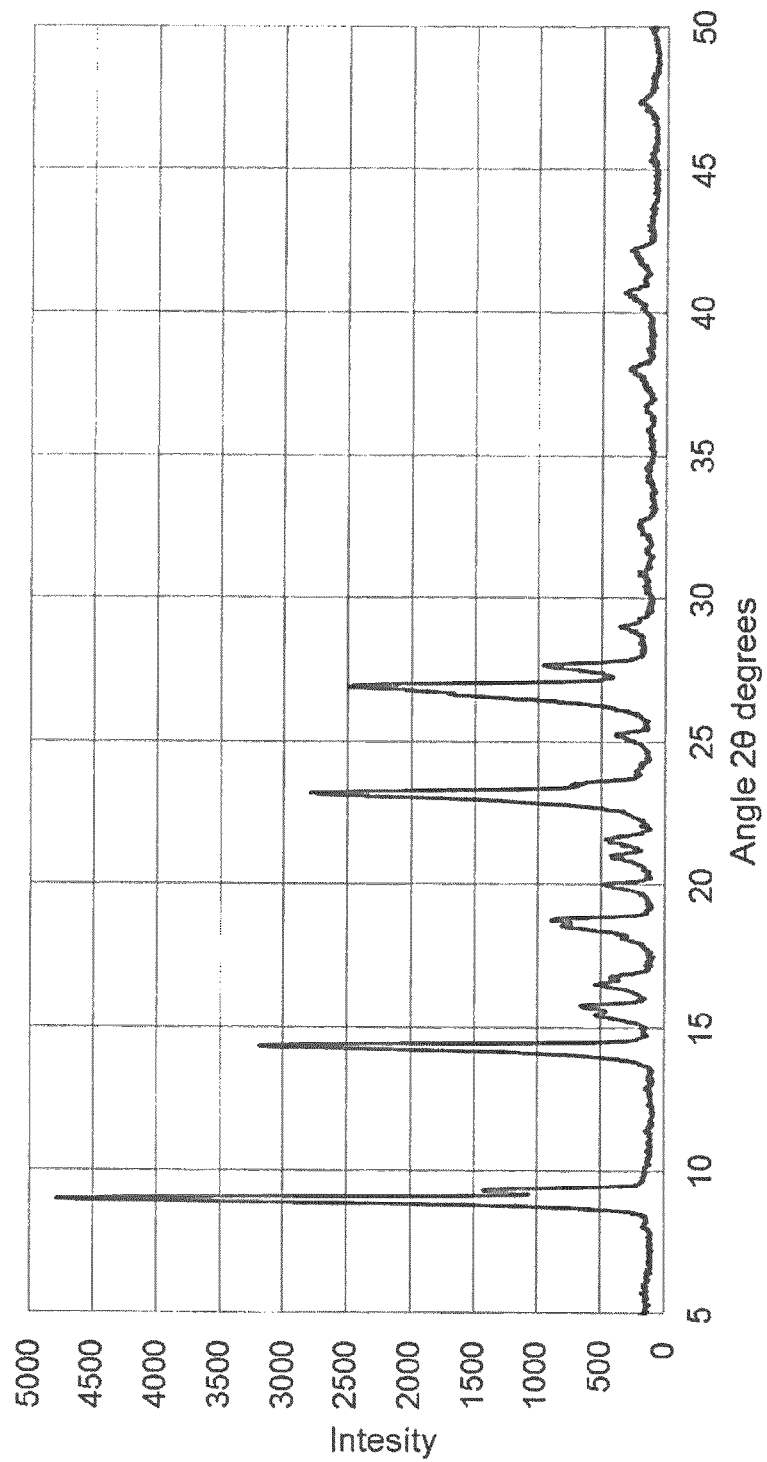
FIG. 6 shows a XRPD pattern for the polymorph of processed ciprofloxacin obtained using the method provided in Example 2 (herein polymorph Form A).
Figure 7:
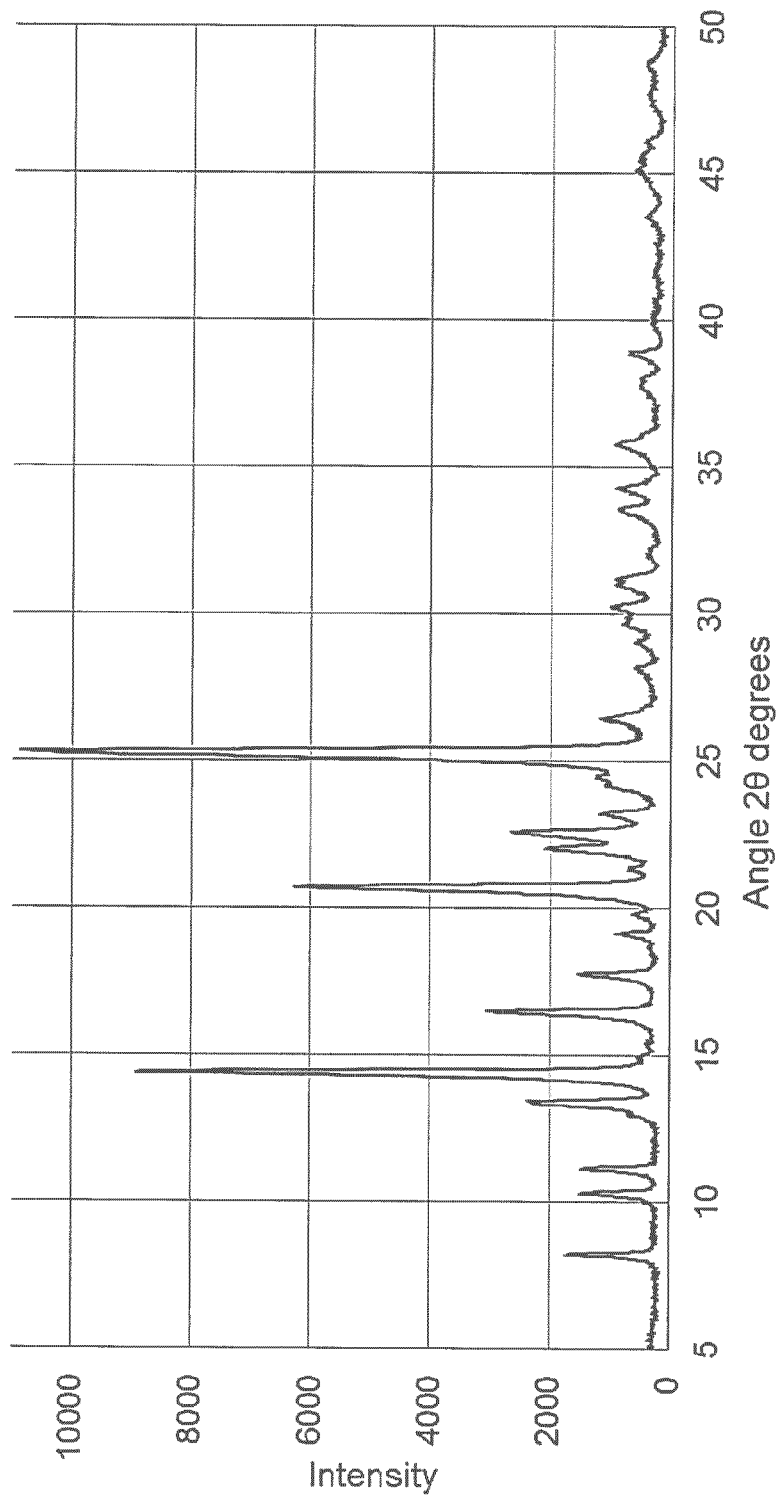
FIG. 7 shows a XRPD pattern for the polymorph of unprocessed, raw ciprofloxacin (Form B).
Figure 8:
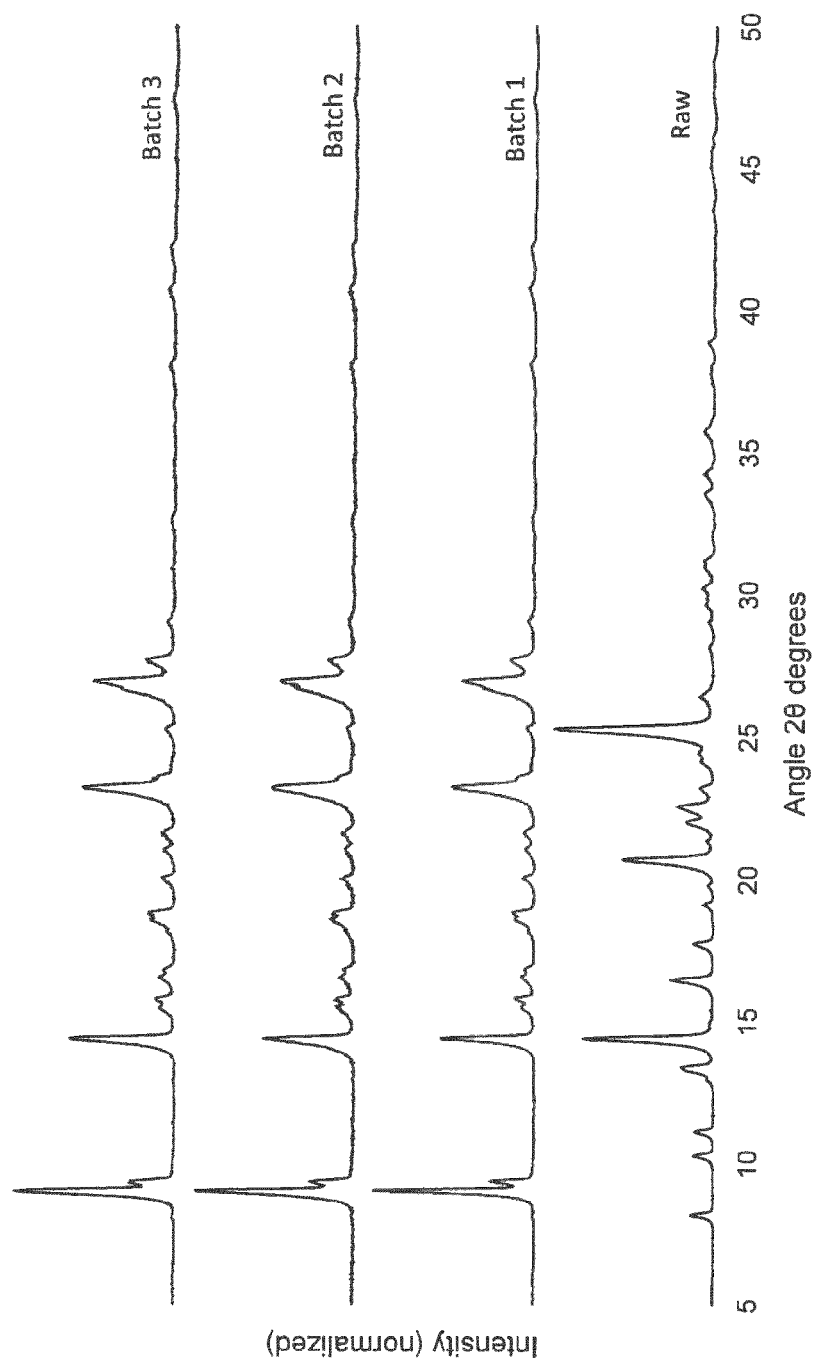
FIG. 8 shows an overlay of the XRPD patterns for the polymorph of unprocessed, raw ciprofloxacin and three batches of the polymorph of processed ciprofloxacin obtained using the method provided in Example 2.

The processed ciprofloxacin particles obtained by this method were also characterized by XRPD. FIG. 6 provides the powder x-ray diffraction pattern for the processed ciprofloxacin produced in Example 2 (polymorph Form A), and FIG. 7 provides the XRPD pattern for the unprocessed, raw ciprofloxacin (polymorph Form B). The direct comparison between the XRPD patterns for the polymorph of unprocessed, raw ciprofloxacin and three batches of the polymorph of processed ciprofloxacin are provided in FIG. 8.

Polymorph Form A (i.e., the processed ciprofloxacin produced in Example 2), shown in FIG. 6, is characterized by the following XRD data:

TABLE 4

| Form A | | |
|---|---|---|
| Reflection No. | Angle 2θ degrees | d-spacing (Å) |
| 1 | 8.161 | 10.8248 |
| 2 | 9.038 | 9.7764 |
| 3 | 9.360 | 9.4414 |
| 4 | 11.535 | 7.6652 |
| 5 | 12.982 | 6.8139 |
| 6 | 14.380 | 6.1544 |
| 7 | 15.480 | 5.7197 |
| 8 | 15.781 | 5.611 |
| 9 | 16.560 | 5.3488 |
| 10 | 18.122 | 4.8911 |
| 11 | 18.800 | 4.163 |
| 12 | 20.041 | 4.4271 |
| 13 | 21.058 | 4.2154 |
| 14 | 21.619 | 4.1073 |

TABLE 4-continued

Form A

| Reflection No. | Angle 2θ degrees | d-spacing (Å) |
|---|---|---|
| 15 | 23.219 | 3.8277 |
| 16 | 24.011 | 3.7033 |
| 17 | 25.300 | 3.5174 |
| 18 | 26.940 | 3.3069 |
| 19 | 27.680 | 3.2202 |
| 20 | 29.041 | 3.0723 |
| 21 | 30.386 | 2.9393 |
| 22 | 30.958 | 2.8862 |
| 23 | 31.701 | 2.8202 |
| 24 | 32.678 | 2.7382 |
| 25 | 34.624 | 2.5886 |
| 26 | 35.937 | 2.4969 |
| 27 | 36.743 | 2.444 |
| 28 | 38.080 | 2.3612 |
| 29 | 40.759 | 2.212 |
| 30 | 42.218 | 2.1389 |
| 31 | 45.479 | 1.9928 |
| 32 | 47.459 | 1.9142 |

Polymorph Form B (i.e., the unprocessed, raw ciprofloxacin), shown in FIG. 7, is characterized by the following XRD data:

TABLE 5

Form B

| Reflection No. | Angle 2θ degrees | d-spacing (Å) |
|---|---|---|
| 1 | 8.201 | 10.7723 |
| 2 | 10.281 | 8.5973 |
| 3 | 11.120 | 7.9503 |
| 4 | 13.399 | 6.6030 |
| 5 | 14.381 | 6.1542 |
| 6 | 14.940 | 5.9250 |
| 7 | 15.399 | 5.7494 |
| 8 | 16.460 | 5.3811 |
| 9 | 17.740 | 4.9955 |
| 10 | 19.103 | 4.6423 |
| 11 | 19.796 | 4.4811 |
| 12 | 20.680 | 4.2916 |
| 13 | 21.338 | 4.1607 |
| 14 | 22.020 | 4.0334 |
| 15 | 22.559 | 3.9381 |
| 16 | 23.199 | 3.8309 |
| 17 | 24.122 | 3.6865 |
| 18 | 25.279 | 3.5202 |
| 19 | 26.420 | 3.3708 |
| 20 | 28.179 | 3.1643 |
| 21 | 29.040 | 3.0724 |
| 22 | 29.641 | 3.0114 |
| 23 | 30.201 | 2.9568 |
| 24 | 31.200 | 2.8644 |
| 25 | 32.039 | 2.7913 |
| 26 | 33.540 | 2.6697 |
| 27 | 34.240 | 2.6167 |
| 28 | 35.760 | 2.5089 |
| 29 | 38.019 | 2.3649 |
| 30 | 38.841 | 2.3167 |
| 31 | 40.667 | 2.2168 |
| 32 | 41.639 | 2.1672 |
| 33 | 42.581 | 2.1215 |
| 34 | 43.501 | 2.0787 |
| 35 | 45.040 | 2.0112 |
| 36 | 45.618 | 1.9870 |
| 37 | 46.061 | 1.9690 |
| 38 | 47.642 | 1.9072 |
| 39 | 48.760 | 1.8661 |

Stability Study

Figure 12:
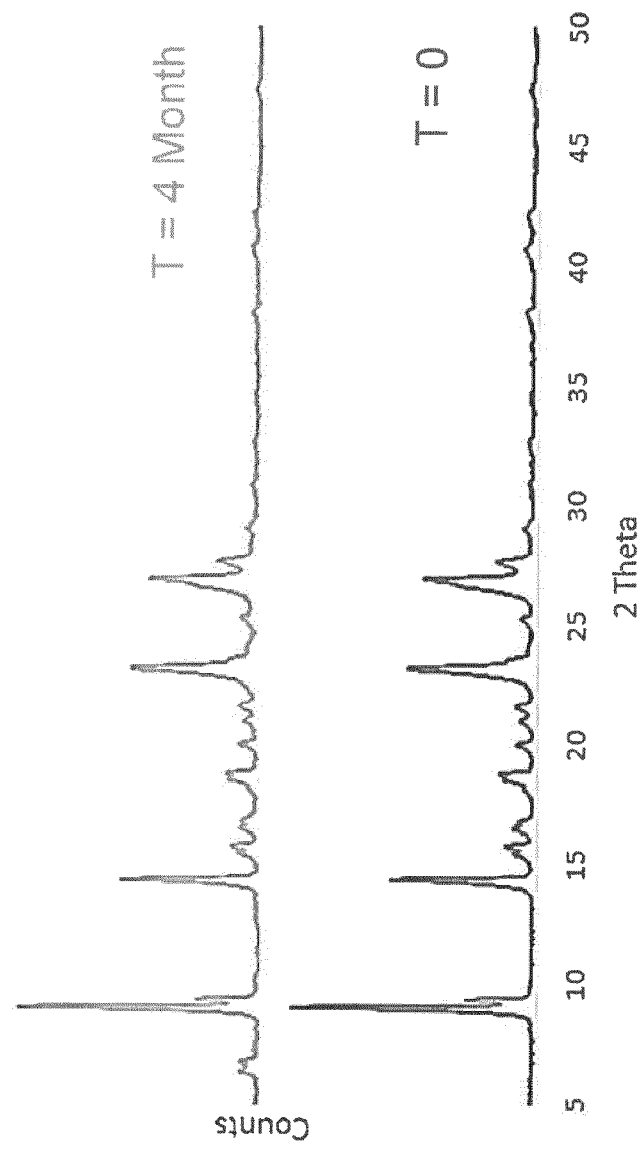
FIG. 12 shows an overlay of the XRPD patterns for the polymorph Form A at the beginning of the storage period (T=0) and after 4 months of storage at room temperature (T=4).

A sample of the processed ciprofloxacin polymorph (Form A) was stored in a closed container at room temperature. Analysis by XRPD, FTIR, and DSC demonstrated that the polymorph was stable after 4 months of storage. FIG. 12 provides an overlay of the XRPD patterns for the polymorph Form A at the beginning of the storage period (T=0) and after 4 months of storage at room temperature (T=4).

Characterization by FTIR

Figure 9:
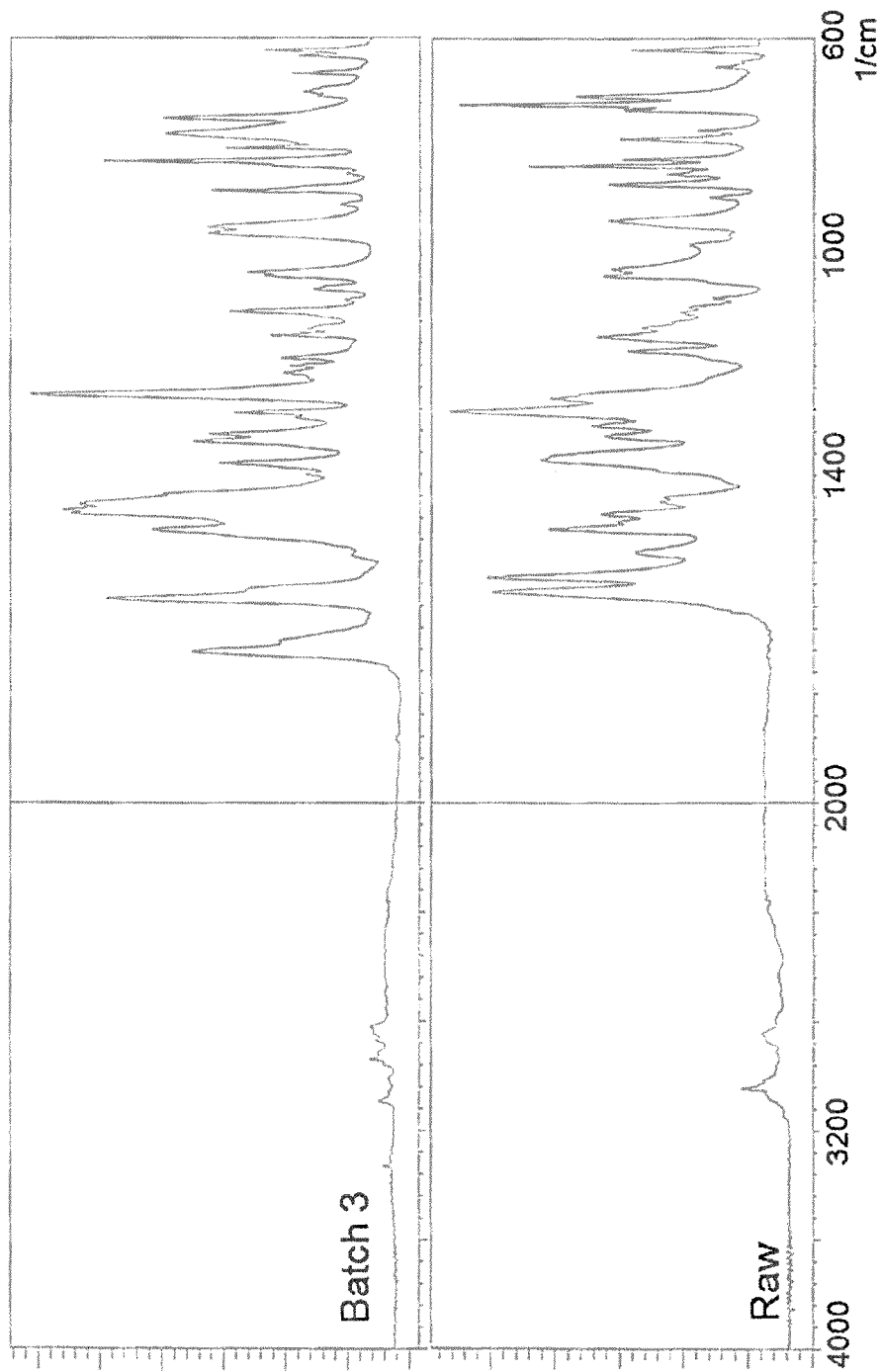
FIG. 9 shows an overlay of FTIR spectrum for the polymorph of unprocessed, raw ciprofloxacin and batch 3 of the polymorph of processed ciprofloxacin obtained using the method provided in Example 2.
Figure 10:
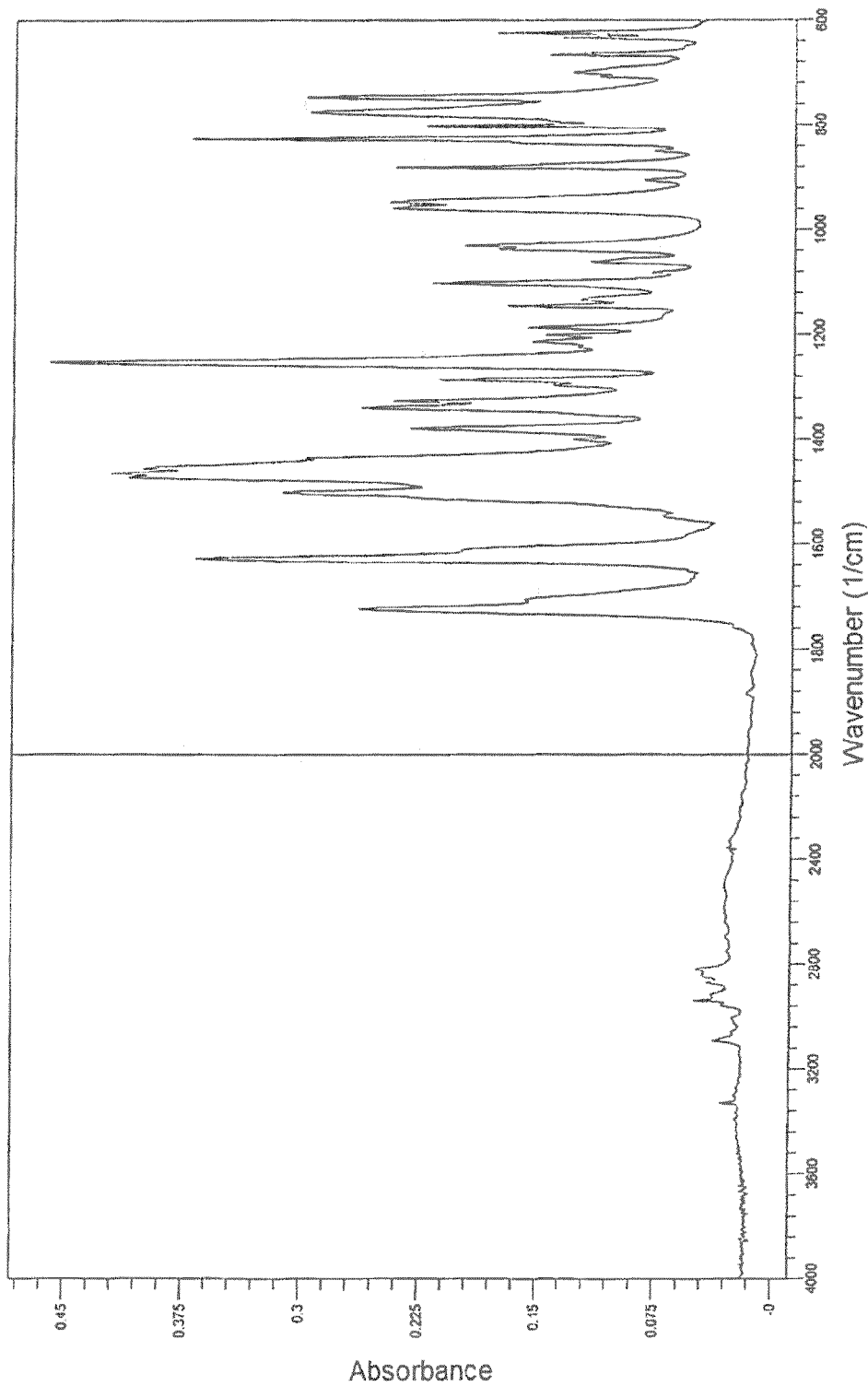
FIG. 10 shows a FTIR spectrum for the polymorph of processed ciprofloxacin obtained using the method provided in Example 2 (polymorph Form A).
Figure 11:
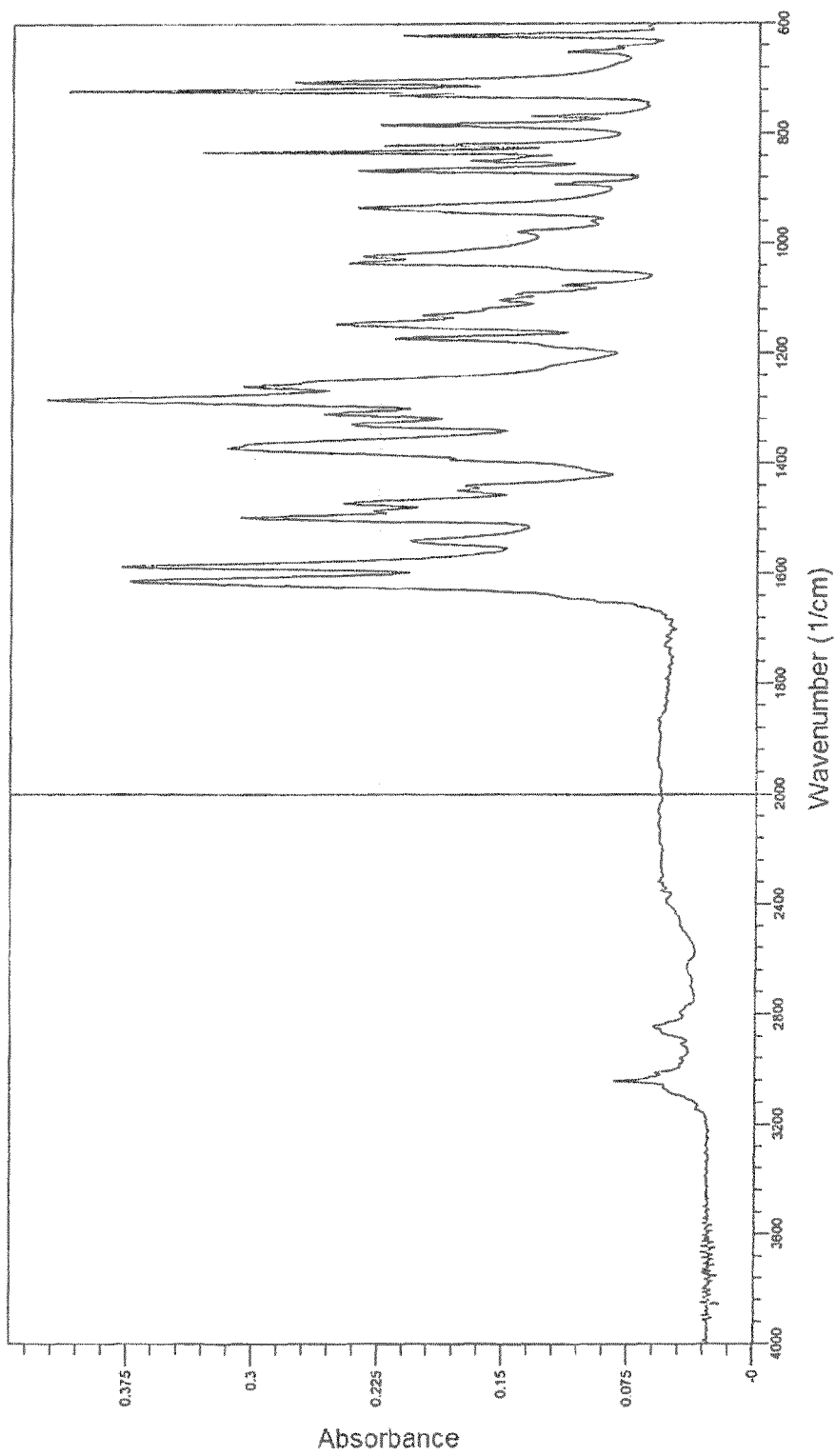
FIG. 11 shows a FTIR spectrum for the polymorph of unprocessed, raw ciprofloxacin (Form B).

The processed ciprofloxacin particles obtained by this method were also characterized by FTIR. FIG. 9 shows an overlay of FTIR spectra for the polymorph of unprocessed, raw ciprofloxacin and the polymorph of processed ciprofloxacin obtained using the method provided in Example 2. FIG. 10 shows a FTIR spectrum for the polymorph of processed ciprofloxacin obtained using the method provided in Example 2 (polymorph Form A), and FIG. 11 shows a FTIR spectrum for the polymorph of unprocessed, raw ciprofloxacin (polymorph Form B).

Polymorph Form A (i.e., the processed ciprofloxacin produced in Example 2), shown in FIG. 10, is characterized by the following FTIR spectrum data:

TABLE 6

Form A

| Peak No. | Wavenumber (cm⁻¹) | Absorbance intensity |
|---|---|---|
| 1 | 623.01 | 0.178398 |
| 2 | 632.65 | 0.13661 |
| 3 | 665.44 | 0.144867 |
| 4 | 700.16 | 0.130025 |
| 5 | 746.45 | 0.299083 |
| 6 | 775.38 | 0.296579 |
| 7 | 802.39 | 0.223149 |
| 8 | 825.53 | 0.371838 |
| 9 | 848.68 | 0.078804 |
| 10 | 879.54 | 0.242667 |
| 11 | 904.61 | 0.084618 |
| 12 | 947.05 | 0.246406 |
| 13 | 958.62 | 0.244465 |
| 14 | 1029.99 | 0.198198 |
| 15 | 1060.85 | 0.118923 |
| 16 | 1080.14 | 0.079478 |
| 17 | 1101.35 | 0.219119 |
| 18 | 1134.14 | 0.124625 |
| 19 | 1143.79 | 0.1712 |
| 20 | 1163.08 | 0.073112 |
| 21 | 1186.22 | 0.157981 |
| 22 | 1201.65 | 0.146678 |
| 23 | 1213.23 | 0.154751 |
| 24 | 1251.8 | 0.461219 |
| 25 | 1284.59 | 0.214473 |
| 26 | 1294.24 | 0.135681 |
| 27 | 1325.1 | 0.243368 |
| 28 | 1338.6 | 0.263193 |
| 29 | 1379.1 | 0.232631 |
| 30 | 1400.32 | 0.128308 |
| 31 | 1435.04 | 0.299007 |
| 32 | 1454.33 | 0.401684 |
| 33 | 1500.62 | 0.313368 |
| 34 | 1546.91 | 0.071895 |
| 35 | 1606.7 | 0.198441 |
| 36 | 1625.99 | 0.368418 |
| 37 | 1703.14 | 0.159326 |
| 38 | 1722.43 | 0.264703 |

Polymorph Form B (i.e., the unprocessed, raw ciprofloxacin), shown in FIG. 11, is characterized by the following FTIR spectrum data:

TABLE 7

| | Form B | |
|---|---|---|
| Peak No. | Wavenumber (cm⁻¹) | Absorbance intensity |
| 1 | 621.08 | 0.212045 |
| 2 | 642.3 | 0.084937 |
| 3 | 651.94 | 0.114122 |
| 4 | 705.95 | 0.277473 |
| 5 | 721.38 | 0.412462 |
| 6 | 767.67 | 0.135829 |
| 7 | 783.1 | 0.225662 |
| 8 | 821.68 | 0.223608 |
| 9 | 833.25 | 0.331853 |
| 10 | 848.68 | 0.171592 |
| 11 | 866.04 | 0.239491 |
| 12 | 891.11 | 0.121806 |
| 13 | 933.55 | 0.239174 |
| 14 | 958.62 | 0.099945 |
| 15 | 977.91 | 0.144005 |
| 16 | 1022.27 | 0.236049 |
| 17 | 1035.77 | 0.245114 |
| 18 | 1076.28 | 0.1176 |
| 19 | 1091.71 | 0.145054 |
| 20 | 1101.35 | 0.154331 |
| 21 | 1118.71 | 0.164865 |
| 22 | 1130.29 | 0.200401 |
| 23 | 1145.72 | 0.252685 |
| 24 | 1172.72 | 0.216865 |
| 25 | 1259.52 | 0.307197 |
| 26 | 1282.66 | 0.424413 |
| 27 | 1309.67 | 0.259305 |
| 28 | 1328.95 | 0.242883 |
| 29 | 1363.67 | 0.306654 |
| 30 | 1371.39 | 0.317656 |
| 31 | 1440.83 | 0.174083 |
| 32 | 1471.69 | 0.247894 |
| 33 | 1496.76 | 0.308945 |
| 34 | 1539.2 | 0.206832 |
| 35 | 1587.42 | 0.379762 |
| 36 | 1612.49 | 0.374669 |
| 37 | 3043.67 | 0.084086 |

Example 3

Antisolvent Crystallization

A drug solution of ciprofloxacin (1-cyclopropyl-6-fluoro-4-oxo-7-(piperazin-1-yl)-1,4-dihydroquinoline-3-carboxylic acid) in HFIP having a concentration of 50 mg/mL was prepared. To the drug solution, 10-mL of antisolvent was added to the samples to precipitate the ciprofloxacin. The individual antisolvents evaluated were methanol, ethanol, isopropyl alcohol, acetone, and ethyl acetate. After precipitation, the sample was dried for approximately 16 hours at 120° C. to remove the residual solvent. The dried ciprofloxacin precipitate was analyzed by XRPD and FTIR. These data showed that ciprofloxacin polymorph A had been formed using all five organic antisolvents. However, the XRPD patterns showed some reflections indicating incomplete drying and removal of residual solvents.

Example 4

Evaporative Crystallization

A drug solution of ciprofloxacin (1-cyclopropyl-6-fluoro-4-oxo-7-(piperazin-1-yl)-1,4-dihydroquinoline-3-carboxylic acid) in HFIP having a concentration of 50 mg/mL was prepared. The drug solution was placed in an oven and heated for approximately 16 hours at 120° C. to precipitate the ciprofloxacin and to remove the residual solvent. The dried material was analyzed by XRPD and FTIR. These data again showed that ciprofloxacin polymorph A had been formed.

The experiment above was also repeated with trifluoroethanol (2,2,2-trifluoroethanol or TFE). Specifically, a drug solution of ciprofloxacin in trifluoroethanol having a concentration of 50 mg/mL was prepared, and placed in an oven and heated for approximately 16 hours at 120° C. to precipitate the ciprofloxacin and to remove the residual solvent. The dried material was analyzed by XRPD and FTIR. These data showed that the polymorph was similar to Form B of the raw ciprofloxacin; the polymorph Form A was not formed.

Example 5

Spray Drying

A drug solution of ciprofloxacin (1-cyclopropyl-6-fluoro-4-oxo-7-(piperazin-1-yl)-1,4-dihydroquinoline-3-carboxylic acid) in HFIP having a concentration of 47 mg/mL was prepared. Buchi B-290 spray dryer was used to spray dry the drug solution. The resulting spray dried material was shown to be amorphous. The amorphous spray dried material was then dried for approximately 16 hours at 120° C. to remove residual solvent. The dried material was analyzed by XRPD and was shown to be crystalline. The crystalline material appeared to be a mixture of polymorph Form B and polymorph Form A.

Example 6

Rat Pharmacokinetics Model

Rat pharmacokinetics (PK) model was used to determine the in-vivo activity of an inhaled formulation of the compositions of the disclosure.

In short, male Charles River Sprague Dawley (CD) Rats, 7-8 weeks old and weighing approximately 150-450 g were used for the study. Prior to the first exposure, animals deemed healthy for the study and acclimated to nose-only exposure tubes were weighed and randomly assigned to study groups by weight stratification. The study groups are outlined in Table 8 below. Animals were then subjected to inhalation or tail vein injection.

TABLE 8

| Group | N | Drug | Target dose (mg/kg) | Admin. | Duration (min) | Necropsy** (hours post dosing) |
|---|---|---|---|---|---|---|
| 1 | 9 | ciprofloxacin | 5 | i.v.* | n/a | 0.5, 6, 12. |
| 2 | 15 | Ex. 1 ciprofloxacin HCl | 3 | Nose-only inhalation | 30 | 0.5, 6, 12, 24, 48 |
| 3 | 15 | Ex. 2 ciprofloxacin | 3 | Nose-only inhalation | 30 | 0.5, 6, 12, 24, 48 |

*i.v. by injection
**3 animals per time point

For the inhalation, the inhalation exposure system was used. The inhalation exposure chamber consists of a rotating brush generator (RBG) (Palas GmbH, Germany) and an exposure chamber with RBG outlet discharging either vertically or horizontally into the exposure chamber. The test drug was packed into a piston. Feed rate was adjusted to achieve the target aerosol concentration. Nose-only exposure tubes were connected directly to the ports on the exposure chamber, and chamber oxygen levels (%) were monitored throughout the exposure.

To monitor the concentration of the drug, the exposure atmospheres were sampled directly from one of the exposure ports onto membrane filters (47-mm GF/A filters, GE Whatman, Pittsburgh, Pa.) at a nominal flow rate through a separate sample line. The concentration was monitored both gravimetrically (e.g., by weighing the filter) and chemically (e.g., by using a high performance liquid chromatography (HPLC)). For the tail vein injections, alert rats were restrained in modified nose-only tubes for lateral tail vein injection. Drug volume was adjusted based on body weight.

Respiratory minute volume (RMV; liters per min) was calculated using the following allometric equation: $RMV=0.608 \, BW^{0.852}$, where BW is the exposure day body weight in kilograms (Alexander et al. *Inhalation Toxicology*: 20 (13): 1179-89. 2008). The estimated dose was calculated using the following formula: Dose=(C×RMV×T×DF)/BW, where C is the average concentration of the test article in the exposure atmosphere, T (min) is exposure time, and the deposition fraction (DF) is assumed to be 10%. Individual animal dose was calculated, and the group average was then estimated.

Animals were examined twice per day (morning and afternoon). At scheduled PK time points or in case of moribund euthanasia, animals were euthanized by intraperitoneal injection of an overdose of a barbiturate-based sedative. After euthanasia, examination was performed on all animals and consisted of a complete external and internal examination including body orifices (ears, nostrils, mouth, anus, etc.) and cranial, thoracic, and abdominal organs and tissues. Blood samples (≤4mL) were then collected into K2EDTA tubes, centrifuged at 1300 g for 10 min at 2-8° C., and plasma analyzed by HPLC. A ±5 min window was allowed for the blood collections. For each animal except those found dead, left and right lungs were grossly examined, weighed separately, and lung tissue sample analyzed by HPLC.

Figure 13:
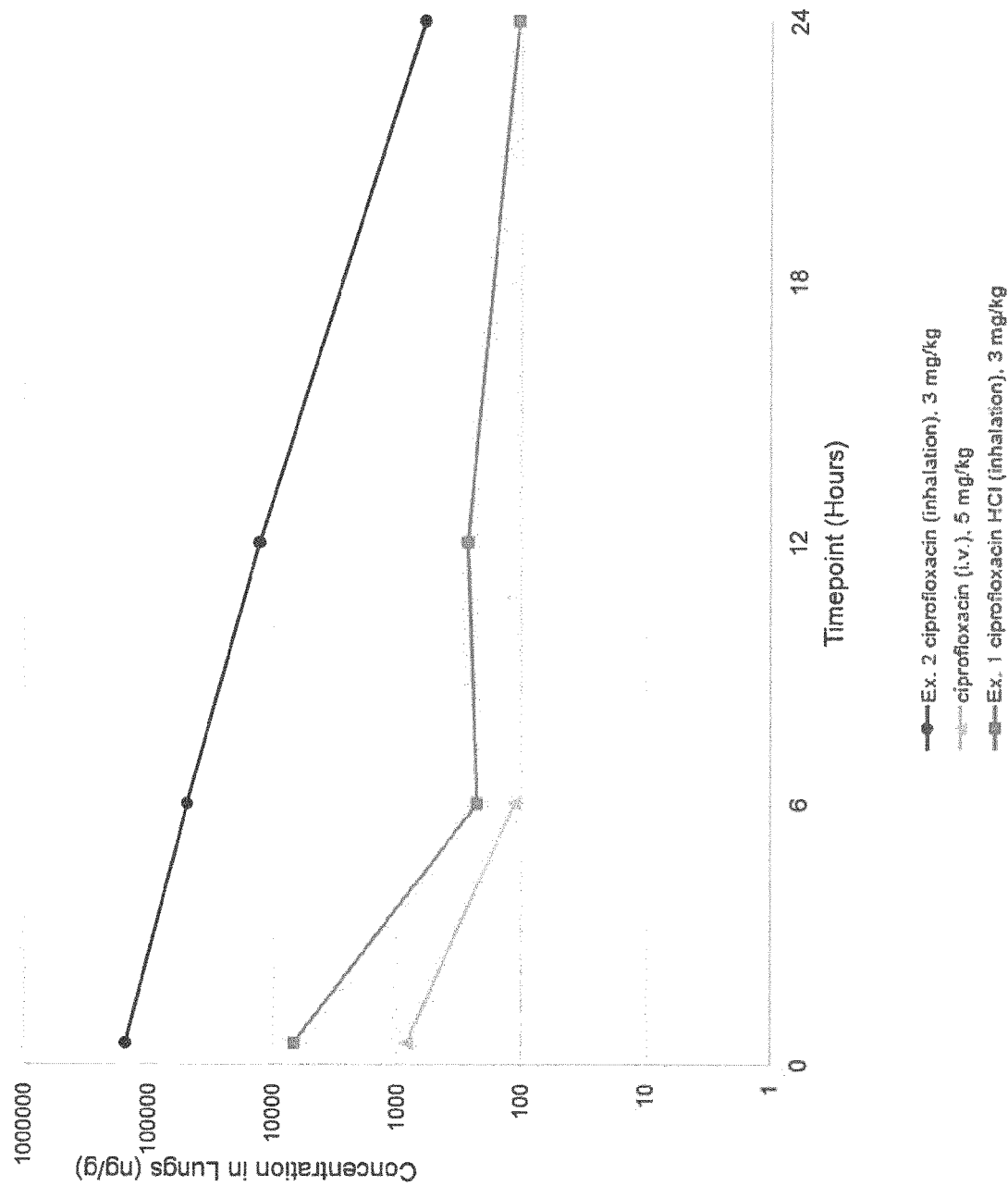
FIG. 13 illustrates ciprofloxacin lung concentration after inhaled administration of ciprofloxacin particle prepared in Example 2 as a dry powder formulation, at a dose of 3 mg/kg of body weight (n=3 rats), after inhaled administration of ciprofloxacin hydrochloride particle prepared in Example 1 as a dry powder formulation, at a dose of 3 mg/kg of body weight (n=3 rats), and after i.v. administration of ciprofloxacin solution formulation at dose of 5 mg/kg of body weight (n=3 rats) in rats.

Table 9 provides the concentration of ciprofloxacin after administration in lungs in each of animal groups. These results are also illustrated in FIG. 13.

TABLE 9

| | Lung concentration (ng/g) | | |
|---|---|---|---|
| Time point (hours) | Ex. 2 ciprofloxacin (inhaled) 3 mg/kg (n = 3) | Ex. 1 ciprofloxacin HCl (inhaled) 3 mg/kg (n = 3) | ciprofloxacin (i.v.) 5 mg/kg (n = 3) |
| 0.5 | 153000 | 6800 | 843 |
| 6 | 48417 | 227 | 113 |
| 12 | 12817 | 271 | BQL* |
| 24 | 607 | 106 | BQL |

*BQL: below quantitation limit

Figure 14:
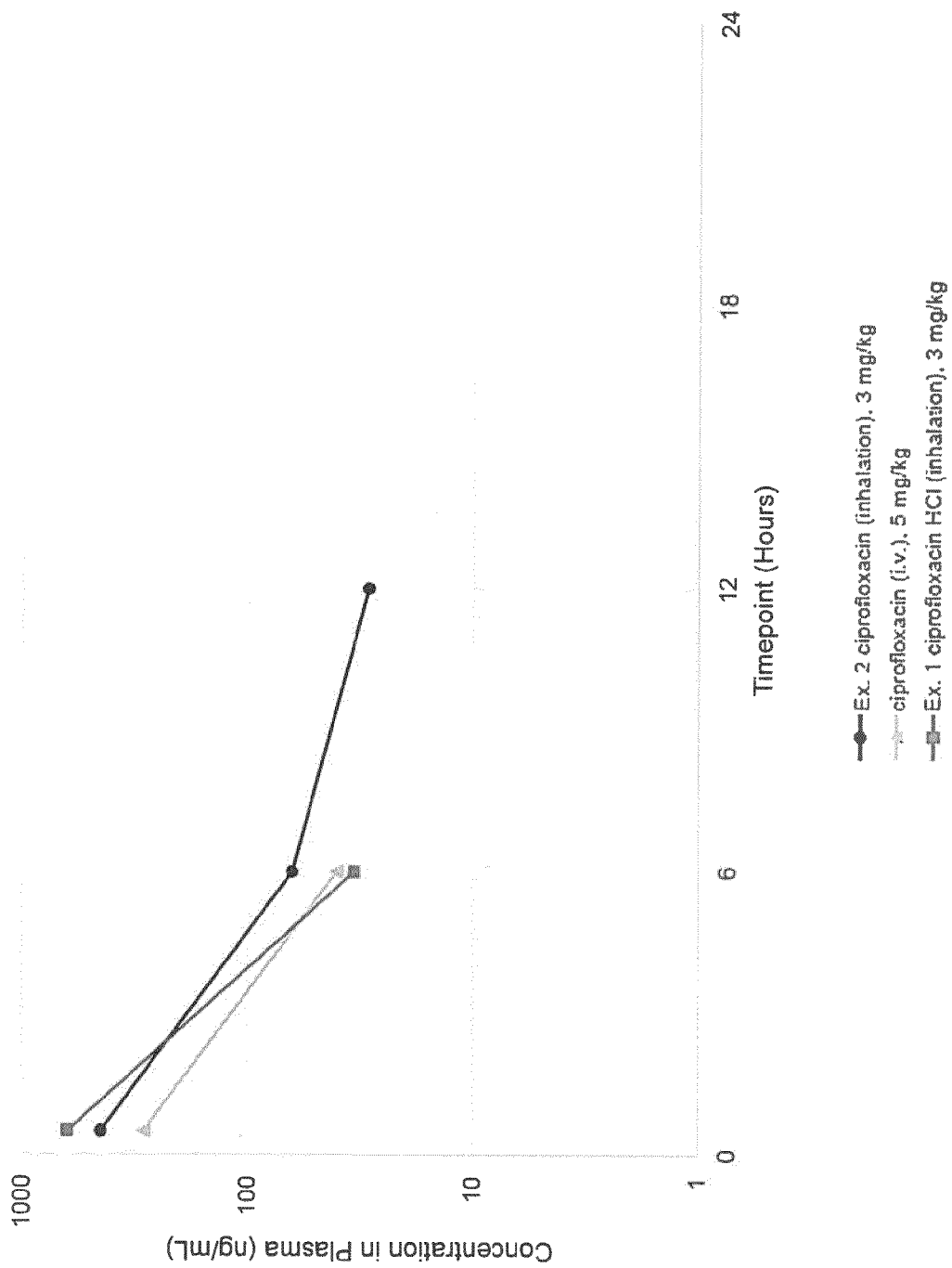
FIG. 14 illustrates ciprofloxacin plasma concentration after inhaled administration of ciprofloxacin particle prepared in Example 2 as a dry powder formulation, at a dose of 3 mg/kg of body weight (n=3 rats), after inhaled administration of ciprofloxacin hydrochloride particle prepared in Example 1 as a dry powder formulation, at a dose of 3 mg/kg of body weight (n=3 rats), and after i.v. administration of ciprofloxacin solution formulation at dose of 5 mg/kg of body weight (n=3 rats) in rats.

Table 10 provides the concentration of ciprofloxacin after administration in plasma in each of animal groups. These results are also illustrated in FIG. 14.

TABLE 10

| | Plasma concentration (ng/g) | | |
|---|---|---|---|
| Time point (hours) | Ex. 2 ciprofloxacin (inhaled) 3 mg/kg (n = 3) | Ex. 1 ciprofloxacin HCl (inhaled) 3 mg/kg (n = 3) | ciprofloxacin (i.v.) 5 mg/kg (n = 3) |
| 0.5 | 447 | 628 | 289 |
| 6 | 63.9 | 33.8 | 40.5 |
| 12 | 29.2 | BQL* | BQL |
| 24 | BQL | BQL | BQL |

*BQL: below quantitation limit

The above-results show that administration by inhalation of ciprofloxacin Form A polymorph (i.e., particles obtained in Example 2) had significantly higher concentrations and longer residence in the lung than the administration of ciprofloxacin hydrochloride particle of Example 1 by inhalation, or i.v. administration of ciprofloxacin formulation solution. But, the plasma levels for these three formulations were similar, indicating similar systemic exposure.

Various aspects of the present disclosure are further exemplified by the non-limiting embodiments recited in the claims below. In each case, features of multiple claims can be combined in any fashion not inconsistent with the specification and not logically inconsistent.

It is understood that the examples and embodiments described herein are for illustrative purposes only and that various modifications or changes in light thereof will be suggested to persons skilled in the art and are to be incorporated within the spirit and purview of this application and scope of the appended claims. All publications, patents, and patent applications cited herein are hereby incorporated herein by reference for all purposes.

What is claimed is:

1. A polymorph of 1-cyclopropyl-6-fluoro-4-oxo-7-(piperazin-1-yl)1,4-dihydroquinoline-3-carboxylic acid characterized in that it provides an XRPD pattern comprising peaks at about 9.0 (2θ degrees), about 23.2 (2θ degrees), about 26.9 (2θ degrees), about 9.3 (2θ degrees), about 18.7 (2θ degrees), about 27.6 (2θ degrees), about 15.48 (2θ degrees), about 15.781 (2θ degrees) about 20.041 (2θ degrees), about 11.535 (2θ degrees), and about 12.982 (2θ degrees).

2. The polymorph of claim 1, characterized in that it provides an XRPD pattern in accordance with that shown in FIG. 6, and/or comprising peaks substantially as set out in Table 4.

3. A composition, comprising particles including the polymorph of claim 1, wherein the particles have a mean particle size (volume-based distribution) in the range of about 0.5 μm to about 10 μm.

4. The composition of claim 3, wherein the particles have a mean particle size (volume-based distribution) in the range of about 0.5 μm to about 7 μm.

5. The composition of claim 3, wherein the particles are uncoated.

6. The composition of claim 3, wherein the composition comprises dry powder or aerosol droplets of the particles, wherein the dry powder or aerosol droplets have a mass median aerodynamic diameter (MMAD) of between about 0.5 μm to about 6 μm diameter.

7. A pharmaceutical composition comprising:
(a) the particles of claim 3; and
(b) a pharmaceutically acceptable carrier.

8. A method for treating a bacterial infection, comprising administering to a subject in need thereof an amount effective to treat the bacterial infection of the composition of claim 3.

9. The method of claim 8, wherein the bacterial infection comprises a bacterial infection selected from the group consisting of infections of bones and joints, endocarditis, gastroenteritis, malignant otitis externa, respiratory tract infections, cellulitis, infectious diarrhea, urinary tract infections, typhoid fever, prostatitis, anthrax, and chancroid.

10. The method of claim 8, wherein the bacterial infection comprises a respiratory tract infection.

11. The method of claim 10, wherein the respiratory tract infection comprises bronchitis and/or pneumonia.

12. The method of claim 8, wherein the composition is delivered via pulmonary administration.

13. The method of claim 12, wherein the pulmonary administration comprises inhalation or nebulization, and wherein the inhalation or nebulization results in pulmonary delivery to the subject of dry powder or aerosol droplets of the composition.

14. The method of claim 12, wherein the composition is administered as a dry powder, or as aerosol droplets having a mass median aerodynamic diameter (MMAD) of between about 0.5 µm to about 6 µm diameter.

15. A method of preparing polymorph particles of claim 3, comprising
 (a) obtaining a solution or a suspension of 1-cyclopropyl-6-fluoro-4-oxo-7-(piperazin-1-yl)-1,4-dihydroquinoline-3-carboxylic acid in a solvent or mixture of solvents;
 (b) feeding and spraying said solution or suspension into a pressurized chamber to obtain a stream of atomized droplets; and
 (c) removing the solvent or mixture of solvents from said droplets to form the polymorph particles.

16. The method of claim 15 wherein the solvent is hexafluoroisopropanol.

17. The method of claim 16, wherein the solution or suspension has concentration of 1-cyclopropyl-6-fluoro-4-oxo-7-(piperazin-1-yl)-1,4-dihydroquinoline-3-carboxylic acid in the range of 10 mg/mL and 100 mg/mL.

18. The method of claim 15, wherein spraying is through a nozzle orifice having a diameter in the range of 20 µm and 125 µm.

19. The method of claim 18, wherein the nozzle orifice is placed between 2 mm and 20 mm from a sonic energy source located within the stream.

* * * * *